(12) United States Patent
Nolan et al.

(10) Patent No.: US 9,463,167 B2
(45) Date of Patent: *Oct. 11, 2016

(54) VISUAL PERFORMANCE AND/OR MACULAR PIGMENTATION

(71) Applicant: Howard Foundation Holdings Limited, Cambridge (GB)

(72) Inventors: John Nolan, Williams Town (IE); Stephen Beatty, Butlertown (IE); James Loughman, Ardclough Staffan (IE); Alan N. Howard, Great Shelford (GB); David Thurnham, Little Wilbraham (GB)

(73) Assignee: Howard Foundation Holdings Limited, Cambridge (GB)

( * ) Notice: Subject to any disclaimer, the term of this patent is extended or adjusted under 35 U.S.C. 154(b) by 64 days.

This patent is subject to a terminal disclaimer.

(21) Appl. No.: 14/618,252

(22) Filed: Feb. 10, 2015

(65) Prior Publication Data

US 2015/0297533 A1 Oct. 22, 2015

Related U.S. Application Data

(63) Continuation of application No. 14/093,929, filed on Dec. 2, 2013, now Pat. No. 8,962,043, which is a continuation of application No. 13/543,287, filed on Jul. 6, 2012.

(30) Foreign Application Priority Data

| Jul. 7, 2011 | (GB) | .................................... 1111624.1 |
| Jul. 7, 2011 | (GB) | .................................... 1111625.8 |
| May 5, 2012 | (GB) | .................................... 1207922.4 |
| May 5, 2012 | (GB) | .................................... 1207923.2 |

(51) Int. Cl.

| A61K 31/047 | (2006.01) |
| A61K 31/07 | (2006.01) |
| A23L 1/30 | (2006.01) |
| A23L 1/302 | (2006.01) |
| A23L 1/304 | (2006.01) |
| A23L 1/32 | (2006.01) |
| A61K 45/06 | (2006.01) |
| A61K 35/57 | (2015.01) |
| A61K 9/48 | (2006.01) |
| A61K 31/202 | (2006.01) |

(52) U.S. Cl.
CPC ........... *A61K 31/047* (2013.01); *A23K 20/179* (2016.05); *A23K 50/75* (2016.05); *A23L 1/3002* (2013.01); *A23L 1/302* (2013.01); *A23L 1/304* (2013.01); *A23L 1/3006* (2013.01); *A23L 1/32* (2013.01); *A61K 9/48* (2013.01); *A61K 31/07* (2013.01); *A61K 31/202* (2013.01); *A61K 35/57* (2013.01); *A61K 45/06* (2013.01); *A23V 2002/00* (2013.01); *A23V 2200/00* (2013.01)

(58) Field of Classification Search
CPC ....................................................... A61K 36/00
USPC ......................................................... 424/725
See application file for complete search history.

(56) References Cited

U.S. PATENT DOCUMENTS

| 6,329,432 B2 | 12/2001 | Howard et al. |
| 2001/0009926 A1 | 7/2001 | Howard et al. |
| 2007/0265351 A1 | 11/2007 | Kumar et al. |
| 2012/0081668 A1 | 4/2012 | Gellerman et al. |

FOREIGN PATENT DOCUMENTS

| EP | 1920711 A1 | 5/2008 |
| KR | 10-2009-0095360 A | 9/2009 |
| WO | 03/063848 A1 | 8/2003 |
| WO | 2005/063223 A1 | 7/2005 |
| WO | 2009/019712 A1 | 2/2009 |

OTHER PUBLICATIONS

Bone et al., "Distribution of Lutein and Zeaxanthin Stereoisomers in the Human Retina," Experimental Eye Research, 64: 211-218 (1997).
Bone et al., "Macular pigment response to a supplement containing meso-zeaxanthin, lutein and zeaxanthin," Nutrition & Metabolism, BioMed Central, 4: 1-8 (2007).
Charalampidou et al., "Prognostic Indicators and Outcome Measures for Surgical Removal of Symptomatic Nonadvanced Cataract," Archives of Ophthalmololgy, 129: 1155-1161 (2011).
Chung et al., Lutein Bioavailability Is Higher from Lutein-Enriched Eggs than from Supplements and Spinach in Men,: Journal of Nutrition, 1887-1893 (2007).
Davison et al., "Macular Pigment: Its Associations with Color Discrimination and Matching," Optometry and Vision Science, 88: 816-822 (2011).
Dhalla et al, "The Macular Automated Photostress Test," American Journal of Ophthalmology, 143: 596-600 (2007).
Goodrow et al., "Consumption of One Egg Per Day Increases Serum Lutein and Zeaxanthin Concentrations in Older Adults without Altering Serum Lipid and Lipoprotein Cholesterol Concentrations," Journal of Nutrition, 2519-2524 (2006).
Hammond et al., "Individual variations in the spatial profile of human macular pigment," Journal of the Optical Society of America, 14: 1118-1196 (1997).
Handleman et al, "Lutein and zeaxanthin concentrations in plasma after dietary supplementation with egg yolk," American Journal of Clinical Nutrition, 70: 247-251 (1999).
Hirsch et al., "The Spatial Resolution Capacity of Human Foveal Retina," Vision Research, 29: 1095-1101 (1989).
International Search Report and Written Opinion issued in related International Patent Application No. PCT/GB2012/051567 dated Oct. 9, 2012.

(Continued)

*Primary Examiner* — Michael Meller
(74) *Attorney, Agent, or Firm* — Morgan, Lewis & Bockius LLP

(57) ABSTRACT

Disclosed is a composition comprising MZ for use as a dietary supplement or food additive for oral consumption for improving the visual performance of a human subject.

1 Claim, 10 Drawing Sheets

(56) References Cited

OTHER PUBLICATIONS

Johnson et al., "Nutritional Manipulation of Primate Retinas, III: Effects of Lutein or Zeaxanthin Supplementation on Adipose Tissue and Retina of Xanthophyll-Free Monkeys," Investigative Ophthalmology & Visual Science, 46: 692-702 (2005).

Khachik et al. "Identification of Lutein and Zeaxanthin Oxidation Products in Human and Monkey Retinas," Investigative Ophthalmology & Visual Science, 38: 1802-1811 (1997).

Kirby et al., "A Central Dip in the Macular Pigment Spatial Profile Is Associated with Age and Smoking," Investigative Ophthalmology & Visual Science, 51: 6722-6728 (2010).

Klaver et al., "Age-Specific Prevalence and Causes of Blindness and Visual Impairment in an Older Population," Archives of Ophthalmology, 116: 653-658 (1998).

Kvansakul et al., "Supplementation with the carotenoids Lutein or Zeaxanthin Improves Human Visual Performance," Ophthalmic and Physiological Optics, 26: 362-371 (2006).

Lorente-Velazquez et al., "Straylight and Contrast Sensitivity After Corneal Refractive Therapy," Optometry and Vision Science, 88: 1245-1251 (2011).

Loughman et al., "The relationship between macular pigment and visual performance," Vision Research, 50: 1249-1256 (2010).

Nolan et al., "The impact of macular pigment augmentation on visual performance in normal subjects: COMPASS," Vision Research, 51: 459-469 (2011).

Seddon et al., "Evaluation of an Iris Color Classification System," Investigative Ophthalmology & Visual Science, 31: 1592-1598 (1990).

Sloane et al., "The Visual Activities Questionnaire: Developing an Instrument for Assessing Problems in Everyday Visual Tasks," Technical Digest, Non-invasive Assessment of the Visual D System, Topical Meeting of the Optical Society of America, 26-29 (1992).

Snodderley et al., "Distribution of Individual Macular Pigment Carotenoids in Central Retina of Macaque and Squirrel Monkeys," Investigative Ophthalmology & Visual Science, 32: 268-279 (1991).

Snodderly et al., "The Macular Pigment. I. Absorbance Spectra, Localization, and Discrimination from Other Yellow Pigments in Primate Retinas," Investigative Ophthalmology & Visual Science, 25: 660-613 (1984).

Stringham et al., "Macular Pigment and Visual Performance in Glare: Benefits for Photostress Recovery, Disability Glare, and Visual Discomfort," Investigative Ophthalmology & Visual Science, 52: 7406-7415 (2011).

Stringham et al., "The utility of using customized heterochromatic flicker photometry (cHFP) to measure macular pigment in patients with age-related macular degeneration," Experimental Eye Research, 87: 445-453 (2008).

van Bree et al., "Straylight Values after Refractive Surgery: Screening for Ocular Fitness in Demanding Professions," Opthalmology, 118: 945-953 (2011).

Wenzel et al., "Macular pigment optical density and photophohia light threshold," Vision Research, 46: 4615-4622 (2006).

Wooten et al., "Spectral Absorbance and Spatial Distribution of Macular Pigment Using Heterochromatic Flicker Photometry," Optometry and Vision Science, 82: 378-386 (2005).

VISUAL PERFORMANCE AND/OR MACULAR PIGMENTATION

CROSS-REFERENCE TO RELATED APPLICATIONS

This application claims priority to U.K. Patent Application No. 1111624.1, filed Jul. 7, 2011; U.K. Patent Application No. 1111625.8, filed Jul. 7, 2011; U.K. Patent Application No. 1207922.4, filed May 5, 2012; U.K. Patent Application No. 1207923.2, filed May 5, 2012; the contents of which are incorporated herein in their entireties.

FIELD OF THE INVENTION

The present invention relates to compositions and methods for improving visual performance in a human subject, and to methods of making the composition.

BACKGROUND OF THE INVENTION

The central retina, known as the macula, is responsible for color and fine-detail vision. A pigment, composed of the carotenoids, lutein (L), zeaxanthin (Z), and meso-zeaxanthin (MZ), accumulates at the macula where it is known as macular pigment (MP). MP is a blue light filter and a powerful antioxidant, and is therefore believed to protect against age-related macular degeneration (AMD), which is now the most common cause of blind registration in the western world. Various scientists have proposed that macular pigments may enhance visual performance (VP), but there does not appear to be any persuasive experimental evidence supporting such hypotheses.

MZ-containing compositions have been disclosed as useful in the treatment of age-related macular degeneration (AMD), see for example U.S. Pat. No. 6,329,432. Supplements containing each of L, Z and MZ are known, and sold for the intended purpose of treating and/or preventing eye disorders such as AMD. One example of such a supplement is sold under the trade mark MacuShield®, and contains the three MP carotenoids L, Z and MZ in the amounts of 10 mg, 2 mg and 10 mg respectively, per dose.

WO 03/063848 discloses the use of a compound, such as lutein, zeaxanthin, mesozeaxanthin or mixtures thereof, for the manufacture of a composition for improving visual performance of a subject in conditions of darkness. The document is, however, rather unusual in that it does not contain any experimental evidence or data to support the alleged use. The person skilled in the art would therefore be rather skeptical of the disclosure and certainly could not derive any expectation of success therefrom.

EP 1 920 711 discloses a method of assessing visual performance which, in effect, involves measuring or determining the amount of macular pigment (such as lutein, zeaxanthin or mesozeaxanthin) present in the subject's eye (i.e. measuring macular pigment optical density, MPOD). If the level of MPOD is low, the document suggests administering a composition comprising lutein and/or zeaxanthin, which is purported to lead to an improvement in visual performance. However, the document does not disclose any actual experimental data to show that improving the level of macular pigment can produce an improvement in visual performance. Again therefore, the person skilled in the art would treat the disclosure of the document with some caution and could not derive any expectation of success therefrom.

SUMMARY OF THE INVENTION

"Dietary supplement" means an addition to the diet in a pill, capsule, tablet, powder or liquid form, which is not a natural or conventional food, and which effectively increases the function of tissues or organs, or increases the level or concentration of a substance in the body, or improves performance of tissues or organs.

The inventors have discovered that consumption of a dietary supplement containing lutein alone has little effect in the MP of subjects who exhibit an abnormally low concentration of MP in the central portion of the retina. In contrast, consumption of a dietary supplement comprising MZ alone can return MP levels in the central portion of the retina substantially to normal, but has little effect on MP levels outside the central portion. Consumption of a combined supplement, containing relatively high amounts of MZ, but also Z and L, cannot only normalize MP levels in the central region of the retina, but also augment MP levels outside the central region of the retina.

For present purposes, the 'central region' of the retina means that central portion of the retina which has an eccentricity of 0.25° or less, as determined by optical coherence tomography (OCT) and/or fundus photography.

In a first aspect the invention provides a composition comprising MZ for use as a dietary supplement, food additive or the like for oral consumption improving the visual performance of a human subject. In preferred embodiments, the subject is a subject without age-related macular degeneration (AMD).

For the purposes of the present specification, a subject is considered to be without AMD if they have a score of 1-3 in the AREDS (Age-Related Eye Disease Study) 11-step maculopathy grading system (Klein et al., 1991 Ophthalmology 98, 1128-1134).

In a second aspect, the invention provides a method of improving the visual performance of a human subject in need of such improvement, the method comprising the step of administering to the subject an effective amount of a composition comprising MZ. As explained below, the composition will preferably also comprise lutein and/or zeaxanthin. The composition will preferably be administered orally, typically as a dietary supplement or food additive. In preferred embodiments the method is performed on a subject without AMD.

An effective amount of the composition for a particular subject can readily be determined by non-inventive routine trial and error, in view of the guidance given in the present specification. Low doses can be given initially and the dosage increased until an improvement in visual performance is detected. The subject's visual performance can be tested in any of a number of convenient methods, as elaborated below.

For present purposes, MZ is understood to refer to the compound (trans,3R,3'S meso)-zeaxanthin, having the structure shown in FIG. 1. Also included within the term "MZ" are esters of MZ, for example the acetate, laurate, myristate, palmitate, linoleate, linolenate and arachidonate esters, and esters with omega 3 fatty acids.

A human subject is considered not to be experiencing AMD if, following examination by a retinologist, there are no signs of any of the following characteristics normally associated with AMD including: soft drusen, hyper- and/or hypo-pigmentary changes at the macula (early AMD), or geographic atrophy or choroidal neovascularisation (advanced AMD).

The composition will preferably comprise MZ at a concentration of at least 0.001% w/w up to 20% w/w. In one embodiment, a preferred concentration of MZ may be in the range 3-10% w/w. However, the person skilled in the art will appreciate that the precise concentration of MZ in the composition of the invention is not critical: a beneficial effect on the visual performance of the subject can be obtained by consuming larger doses of a composition comprising lower concentrations of MZ and vice versa. A typical effective average daily dose of MZ to be consumed by a normal human adult subject will typically be in the range 0.1 mg to 100 mg per day, more conveniently in the range 1 to 50 mg per day, and preferably in the range 5-25 mg per day.

The composition may conveniently be in unitary dosage form e.g. as a tablet, capsule or the like. Conveniently, but not necessarily, the composition may be packaged in a foil blister pack, of the sort known to those skilled in the art. Desirably one or two of the doses are taken each day, the amount of MZ in the doses being adjusted accordingly.

The composition of the invention will desirably comprise not only MZ, but also lutein and/or zeaxanthin. Most preferably the composition will comprise MZ, lutein and zeaxanthin, which may be collectively referred to as macular carotenoids. Conveniently, but not necessarily, MZ will be present in the composition at a greater concentration or the same concentration as lutein or zeaxanthin. The percentage of either MZ or lutein in the composition can range from 10% to 90% (of macular carotenoid pigment present in the formulation). The percentage of zeaxanthin can typically range from 5 to 45% (of macular carotenoid pigment in the formulation). A particularly favored composition has an MZ:lutein:zeaxanthin ratio of 10:10:2 (or 45%, 45%, 10%).

The three macular carotenoids may be combined or preferably manufactured as such in single formulation. The composition of the invention may be in any formulation suitable for oral consumption by a human subject, including a tablet, capsule, gel, liquid, powder or the like. The macular carotenoids may be granulated for example as microcapsules before inclusion in the formulation. The composition may conveniently comprise conventional diluents, especially vegetable oils such as sunflower, safflower, corn oil and rape seed oils, excipients, bulking agents and the like which are well known to those skilled in the art. Such substances include calcium and/or magnesium stearate, starch or modified starch.

Other conventional formulating agents may be present in the composition, including any one or more of the following non-exclusive list: acidity regulators; anticaking agents (e.g. sodium aluminosilicate, calcium or magnesium carbonate, calcium silicate, sodium or potassium ferrocyanide), antioxidants (e.g. vitamin E, vitamin C, polyphenols), colorings (e.g. artificial colorings such as FD&C Blue No. 1, Blue No. 2, Green No. 3, Red No. 40, Red No. 3, Yellow No. 5 and Yellow No. 6; and natural colorings such as caramel, annatto, cochineal, betanin, turmeric, saffron, paprika etc.); color retention agents; emulsifiers; flavors; flavor enhancers; preservatives; stabilizers; sweeteners and thickeners.

The above-mentioned compositions containing MZ can be an added to a preparation containing essential vitamins and minerals; for example a one a day tablet/capsule containing all RDAs of the vitamins and minerals required by man; or dietary products which are fortified by vitamins and minerals; or together with omega 3 fatty acids.

Macular carotenoids containing MZ can be fed to hens and the eggs therefrom can provide an excellent source of MZ for human consumption Visual Performance Visual performance is a state, condition or parameter, not an abnormality or a disease. Thus there is a range of values in normal subjects without the presence of any underlying retinal or macular disease. However, like all other human conditions, improvements in VP are considered beneficial and desirable.

There are many different measures of "visual performance" known to those skilled in the art.

For present purposes, improving "visual performance" means producing a detectable improvement in one or more of the following in the subject: contrast sensitivity; visual acuity, preferably best corrected visual acuity; glare disability; discomfort glare; ocular straylight; photostress recovery; and S-cone sensitivity. Preferably the improvement in visual performance created by consumption of the composition of the invention comprises an improvement in one or more of: contrast sensitivity, best corrected visual activity, or glare disability.

Preferably consumption of the composition of the parameters of visual performance, more preferably in two or more, and most preferably a detectable improvement in three or more of the aforementioned visual performance parameters.

The various parameters of visual performance listed above are described in more detail below.

(i) Contrast Sensitivity Function

Contrast is the difference in visual properties that make an object (or its representation in an image) distinguishable from other objects and the background. In visual perception of the real world, contrast is determined by the difference in the color and brightness of the object and other objects within the same field of view. Contrast Sensitivity is a measure of a subject's sensitivity to changes in contrast; it is a measure of how much contrast is required to accurately detect a target as distinct from its background.

By altering the size (spatial frequency) of a target, and the luminance of the background, it is possible to test Contrast Sensitivity function, which is very much reflective of real-world vision, where the most important determinants of vision are contrast, size and luminance. Contrast Sensitivity function can be assessed using the Functional Acuity Contrast Test (FACT), which is designed to test contrast sensitivity at varying spatial frequency settings, as disclosed by Loughman et al., 2010 Vision Res. 50, 1249-1256). Letter Contrast Sensitivity may be measured using the commercially available "Thomson Chart".

(ii) Visual Acuity

Visual acuity is a simple and intuitive way of assessing visual performance It is a useful measure of vision because it relates directly to the need for spectacles (i.e. if an individual is long or short sighted, the introduction of spectacle lenses typically creates a predictable improvement in visual acuity). Also, it tends to be adversely affected by ocular disease and therefore abnormal visual acuity can be a sign of developing abnormality.

Despite its widespread use and popularity, it is not the best technique for the assessment of vision because (a) it tends not to relate well with vision in conditions different to the brightly lit, high contrast test environment, and (b) it only evaluates performance at the high spatial frequency (i.e. small letter size) end of the spectrum. Typically best corrected visual acuity ("BCVA") is assessed using a high contrast (close to 100%, i.e. black letters on a white background) letter chart, after the subject's vision has been corrected with corrective lenses to the best level possible. The subject's task is to read the smallest possible letter size they can recognize. The visual performance is quantified using a standard notation (e.g. Snellen notation; where 20/20 or 6/6 vision is accepted as normal human vision). Improvements in BCVA imply a benefit in visual acuity in general.

(iii) Glare Disability

Glare disability is a term used to describe the degradation of visual performance typically caused by loss of retinal image contrast. Glare disability is often caused, for example, by surface light reflections, or bright light sources such as car headlights, and typically is a consequence of increased forward light scatter within the eye. New bi-xenon high intensity discharge ("HID") car headlights contain more "blue" light and are often considered as a cause of additional glare disability compared to older headlight sources.

This is of particular importance to macular pigment investigations because of the optical filtration properties of macular pigment. Macular pigment acts as a short wavelength (blue) light filter. Its prereceptoral and central location facilitate the optimization of visual performance with respect to glare because intraocular forward light scatter is short wavelength (blue) light dominated.

Glare disability can be assessed using the Functional Acuity Contrast Test (FACT), as disclosed by Loughman et. al., 2010 Vision Res. 50, 1249-1256.

(iv) Discomfort Glare

Discomfort glare results in an instinctive desire to look away from a bright light source or difficulty in seeing a task. It refers to the sensation one experiences when the overall illumination is too bright e.g. on a snow field under bright sun.

Macular pigment has the capacity to diminish the effects of discomfort glare because (a) it filters the blue component which contains most energy; less light and less energy therefore reach the photoreceptors to affect performance, and (b) macular pigment also has dichroic properties which means it has the capacity to filter plane polarized light. Plane polarized light is light reflected from a surface (e.g. snow covered ground, water etc) into the eye. It is unidirectional so the energy is concentrated and therefore has increased effect on vision. This is why skiers, anglers and the like wear polarized sunglasses to reduce such discomfort glare.

Discomfort glare is assessed using a discomfort rating scale as disclosed by Wenzel et al., 2006 Vision Res. 46, 4615-4622.

(v) Ocular Straylight

Ocular straylight is a parameter that is relatively new in clinical practice after being studied for many years in experimental settings. It concerns the part of the incident light that is scattered by the ocular media and does not participate in the normal image formation on the retina. Instead, this light creates a more or less homogeneous haze over the retinal image. Several pathologies are known to increase retinal straylight considerably, which may lead to symptoms such as loss of contrast sensitivity, disability glare, and halos. This will reduce a patient's quality of vision in everyday life, for example while driving at night and recognizing a person against a light source, but has only a very limited effect on visual acuity as measured during an ophthalmic examination.

As macular pigment absorbs the dominant short wave scattered component, it has the capacity to significantly reduce the amount of ocular straylight, and therefore further enrich visual performance particularly under circumstances of glare.

Ocular stray light is assessed using the Oculus C-Quant as disclosed by van Bree et al., 2011 Ophthalmology 118, 945-953.

(vi) Photostress Recovery

Photostress Recovery testing is a method of assessing visual performance by timing the recovery of visual function after adaptation to an intense light source. The test involves exposing the macula to a light source bright enough to bleach a significant proportion of the visual pigments. Return of normal retinal function and sensitivity depends on the regeneration of the visual pigments. The test essentially provides an indirect assessment of macular function.

Photostress recovery is assessed using a macular automated photostress test using the Humphrey Perimeter as disclosed by Loughman et. al., 2010 Vision Res. 50, 1249-1256.

(vii) S-cone Sensitivity

S-cones are the "blue" sensitive cones i.e. their peak sensitivity is to short wavelengths. Typically, a person with high levels of macular pigment would be expected to demonstrate low S-cone sensitivity, as the macular pigment is minimizing the amount of blue light striking the photoreceptors. Combining a test of S cone sensitivity with a photostress test can provide information on the direct effects of macular pigment on the actual sensitivity of those cones most affected by glare.

S-cone sensitivity is assessed using the short-wavelength automated perimetry program (SWAP) on the Humphrey Perimeter as described by (Davison et. al., *Optom. Vis. Sci.* 2011 vol. 88).

(viii) Assessment of VP by Questionnaire

Another method of testing for improvement in visual performance is the use of a questionnaire to score the subject's own assessment of their visual performance. In preferred embodiments of the invention therefore, a detectable improvement in visual performance is determined by an increased score in a subjective assessment questionnaire following a suitable period of weeks or months of consumption of the composition, as compared to a control assessment questionnaire completed prior to commencing consumption of the composition.

A suitable questionnaire is disclosed by Charalampidou et al., Arch. Ophthalmol. 2011 (May 9, Epublication ahead of print), in which is described a 30-part, non validated, "Visual Function in Normals" questionnaire (VFNq30), which was designed to assess subjective visual performance improvement. The design was based in part on a previously-validated visual activities questionnaire (Sloane et al., "The Visual Activities Questionnaire: Developing an instrument for assessing problems in everyday visual tasks. Technical Digest, Non-invasive Assessment of the Visual System, Topical Meeting of the Optical Society of America 1992), but adapted to suit a normal, young and healthy population sample. This questionnaire allows the subject to quantify their visual performance using three separate metrics: situational analysis (SA) which requires the subject to rate their visual performance in specified daily life situations; comparative analysis (CA) which requires the subject to compare their perceived visual performance to that of their peers/family/friends; subject satisfaction score (SSS) which requires the subject to provide an overall estimate of their perceived quality of vision. Each of the three metrics above is computed to give a performance score for five different functional aspects of their vision: acuity/spatial vision: glare disability; light/dark adaptation; daily visual tasks; and color discrimination.

Time to Achieve an Improvement of VP

Obviously, one does not expect any measurable, discernible or detectable improvement in the visual performance of a subject immediately after consuming the composition of the invention. The period of dietary supplementation required to produce a measurable improvement in visual performance will depend on several factors, including the average daily dose size of the macular carotenoids in the subject prior to commencing dietary supplementation, the subject's general health etc. Typically one would expect to require dietary supplementation with the composition of the invention for at least 8 weeks, and more preferably at least 3 or 6 months before measuring one or more visual performance parameters to test for any improvement therein.

The subject may need to consume the active composition of the invention at least once a week, more normally at least 3 times a week, and preferably daily.

Preferred Embodiments

In one embodiment of the invention, the composition may be consumed by subjects who have a deficiency in the amount of macular pigment in the central portion of their macula. By way of explanation the inventors have found that there exists a proportion of the population at large who may not be experiencing AMD (as herein defined), but who possess statistically significantly lower levels of macular pigment in the centre of the macula as determined by customized heterochromatic flicker photometry (cHFP) using the Macular Densitometer™. These subjects are described as having an atypical macular pigment distribution, referred to as a "central dip". Using this technique, MP may be measured psychophysically by HFP. HFP is based on the fact that MP absorbs blue light. The subject may be asked to observe a target, within a test field, which is alternating in square wave counterphase between blue (460 nm) and green light (550 nm), i.e. flickering. They must adjust the luminance of the blue light to achieve null flicker, in other words, until the target becomes steady. The ratio of the amount of blue light required to achieve null flicker at the fovea may be compared to that required in the para-fovea (where MP is presumed to be zero), the logarithm of which is known as optical density. Using the Densitometer, MP can be measured at five points across the macula; 0.25°, 0.5°, 1°, 1.75° and 7°. The principle of HFP remains the same for each target. For those retinal eccentricities outside the fovea, i.e. 0.5°, 1°, 1.75° and 7°, the fixation point may be placed at the desired angular distance from a flickering disc. Three measurements may be taken at each loci and an average calculated. To minimize error in the HFP settings, care may be taken to optimize the flicker rate for each subject, otherwise known as critical flicker frequency (CFF). CFF is the frequency at which the subject can no longer perceive flicker in a 0.5° target at 550 nm. The CFF may be determined with a method of limits by which the flickering frequency is progressively decreased (or increased), until the subject reports a change from fusion to flicker (or flicker to fusion). Subjects with an atypical macular pigment distribution ("central dip") may have an MPOD at 0.5° eccentricity which is greater than or equal to the MPOD at 0.25° eccentricity.

In another embodiment, the composition may be consumed by subjects who have statistically normal levels of macular pigment.

In another embodiment, the invention may provide a method of making a composition for human consumption, the composition to be consumed by a human subject for the purpose of improving visual performance, the method comprising the step of mixing an effective amount of MZ with an acceptable dietary diluent, excipient or carrier. The method may additionally comprise the addition of lutein and/or zeaxanthin to the diluent, excipient or carrier (or vice versa). Performance of the method may desirably result in manufacture of a composition having the preferred features set forth above. The method may additionally comprise the step of packaging the composition in a package together with instructions for consumption of the composition to effect an improvement in visual performance Conveniently, the composition may be packaged in unitary dose form e.g. as a plurality of tablets, capsules or pills, which may be packaged loose (e.g. in a tub) or may be packaged individually (e.g. in a blister pack).

In one particular embodiment, the invention may provide a method of improving the visual performance of a human subject, the method comprising the steps of:
  a) supplying a feed to egg-laying birds, such as hens or ducks, which feed comprises MZ, so as to cause the birds to lay eggs comprising MZ;
  b) collecting said eggs, and supplying the eggs, or at least part of the yolk thereof, in edible form to the subject.

Whole eggs may be provided raw for cooking by the subject. Alternatively the eggs may be processed and at least part of the yolks thereof provided to the subject, the MZ content of the eggs being concentrated in the yolk. Processing may involve, for example, shelling, cooking and drying the eggs.

Typically the composition of the invention may be consumed at least once a week, preferably at least twice a week, more preferably at least three times a week, and most preferably at least daily. In some embodiments the composition may be consumed more than once a day (e.g. once in the morning and once in the evening). The person skilled in the art will appreciate that the frequency of consumption can be adjusted to take account of the concentration of macular pigment carotenoids, especially meso-zeaxantion, present in the formulation. The method of the invention can be adjusted accordingly.

Consuming the composition of the invention, or performing the method of invention, over a sufficient period of time (typically at least 8 weeks, preferably at least 3 months, more preferably over at least 6 months, and most preferably for 12 months or more) may typically result in an increase in the level of macular pigment in a subject.

The amount of increase in the level of macular pigment carotenoids in the subject which is achieved by consumption of the composition may depend on, for example, the level of macular pigment carotenoids present in the subject's eyes prior to commencement of consumption of the composition. As described above, the inventors have found that there is a proportion of the population (about 10% or so) in Ireland which have abnormally low levels of macular pigment and an abnormal distribution of carotenoid pigments within the macula, and it is anticipated that similar subjects exist in other populations. Such people might be expected to exhibit a substantial increase in the level of macular pigment following long term (i.e. 6 months or more) consumption of the composition of the invention.

Significantly, however, and surprisingly, the inventors have also found that at least some parameters of visual performance (e.g. letter contrast sensitivity; glare disability) can be improved by consumption of the composition of the invention without necessarily a corresponding increase in the level of macular pigment.

In particular, the composition/method of the invention can produce a detectable improvement in the visual performance of a subject in conditions other than low light. For example, the composition/method of the invention can produce an improvement in the visual performance of a subject in conditions of illumination greater than 1 $Cdm^{-2}$; more especially in photopic conditions (e.g. illumination levels greater than or equal to 3 $Cdm^{-2}$).

More especially, the composition/method of the invention can produce an improvement in one or more of the following visual performance parameters: visual acuity, especially best corrected visual acuity (BCVA); contrast sensitivity (CS); and glare disability (GD). Suitable methods of measuring these visual performance parameters are known to those skilled in the art and are described in detail herein. Typically the method/composition of the invention will produce an improvement of at least 5%, preferably at least 8%, more preferably at least 10%, relative to the same parameter measured prior to consumption of the composition/performance of the method of the invention.

For the avoidance of doubt it is hereby explicitly stated that any feature of the invention described herein as preferable, advantageous, convenient, desirable, typical or the like may be present in any embodiments of the invention in isolation, or in any combination with any one or more other such features, unless the context dictates otherwise. In addition, features described in relation to one aspect of the invention will equally apply to the other aspects of the invention, unless the context dictates otherwise.

The content of all publications and citations mentioned in this specification is specifically incorporated herein by reference.

BRIEF DESCRIPTION OF THE DRAWINGS

The invention will now be further described by way of illustrative embodiment and with reference to the accompanying drawings, in which.

DETAILED DESCRIPTION OF PREFERRED EMBODIMENTS

EXAMPLE 1

Comparison of Macular Responses after Supplementation with Three Different Macular Carotenoid Formulations Subjects and Recruitment This study was conducted at the Institute of Vision Research, Whitfield Clinic, Waterford, Republic of Ireland. Seventy one subjects volunteered to participate in this study, which was approved by the local research ethics committee. Subjects were aged between 32 to 84 years and in good general health. The volunteers were divided into two groups: an AMD group and a normal group. 34 subjects had confirmed early stage AMD in at least one eye (AMD group; categorized and identified by either presence of drusen and/or pigmentary changes at the macula), and 37 subjects had no ocular pathology (normal group). Importantly, for the AMD group, significant efforts were made to identify patients with early AMD who were not currently taking carotenoid supplements.

Study Design and Formulation

L=Lutein MZ=mesozeaxanthin Z=Zeaxanthin

This study was a single blind, randomized-controlled clinical trial of oral supplementation with three different macular carotenoid formulations, as follows:

Group 1: High L Group
 (n=24 [normal group=12 and AMD group=12];
 L=20 mg/day, Z=2 mg/day);

Group 2: Mixed Carotenoid Group
 (n=24 [normal group=13 and AMD group=11];
 MZ=10 mg/day, L=10 mg/day, Z=2 mg/day);

Group 3: High MZ Group
 (n=23 [normal group=12 and AMD group=11];
 MZ=18 mg/day, L=2 mg/day L).

All subjects were instructed to take one capsule (oil based) per day with a meal for 8 weeks. Compliance was assessed by tablet counting at each study visit.

Measurement of Macular Pigment Optical Density (MPOD)

The spatial profile of MP was measured using customized heterochromatic flicker photometry (cHFP) using the Macular Densitometer™, a cHFP instrument that is slightly modified from a device described by Wooten & Hammond (2005 Optometry & Vision Science 82, 378-386) and by Kirby et al., (2010 Invest. Ophthalmol. Vis. Sci. 51, 6722-6728.

Subjects were assessed at baseline, two weeks, four weeks, six weeks, and 8 weeks (V1, V2, V3, V4, and V5, respectively). MPOD was measured at the following eccentricities: at 0.25°, 0.5°, 1°, 1.75°, 3° but only results at 0.25°, the central part of the retina corresponding to the macula, are reported here.

Statistical Analysis The statistical software packages PASW Statistics 17.0 (SPSS Inc., Chicago, Ill., USA) and R were used for analysis and Sigma Plot 8.0 (Systat Software Inc., Chicago, Ill., USA) was used for graphical presentations. All quantitative variables investigated exhibited a typical normal distribution. We used the 5% level of significance.

Results

MPOD and Visual Acuity

Figure 1:
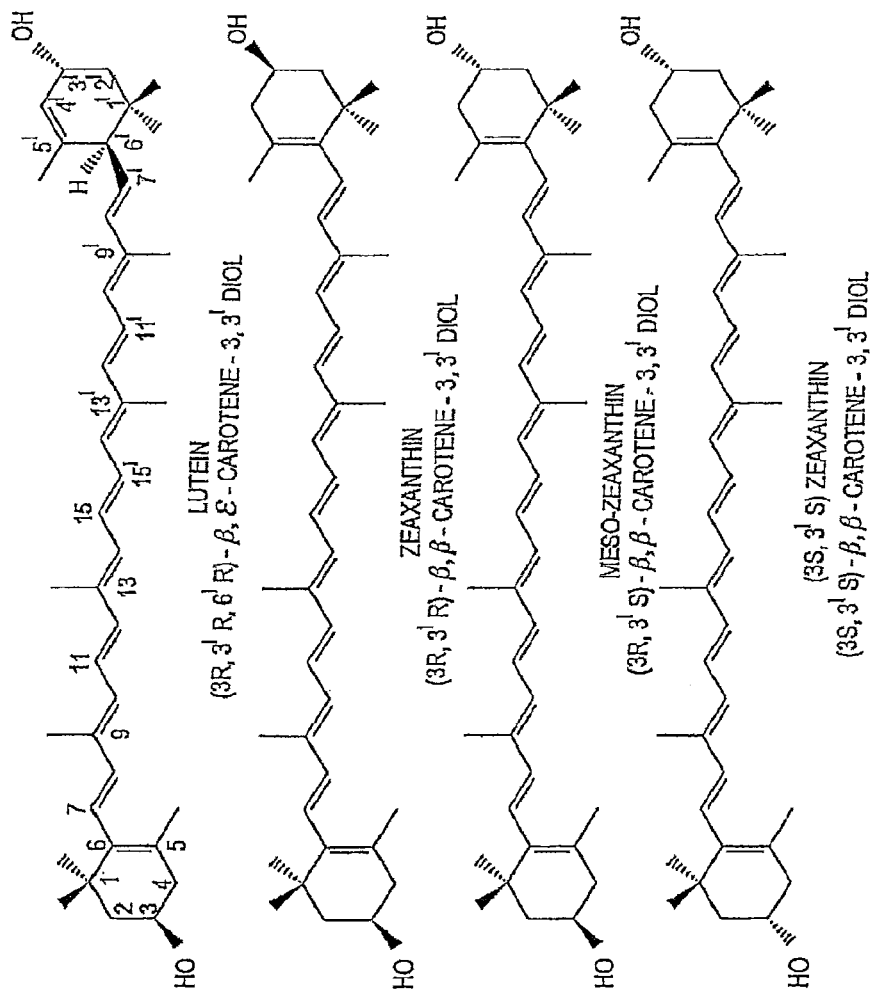
FIG. 1 is a schematic representation of the structural formulae for lutein, zeaxanthin and MZ.
Figure 2:
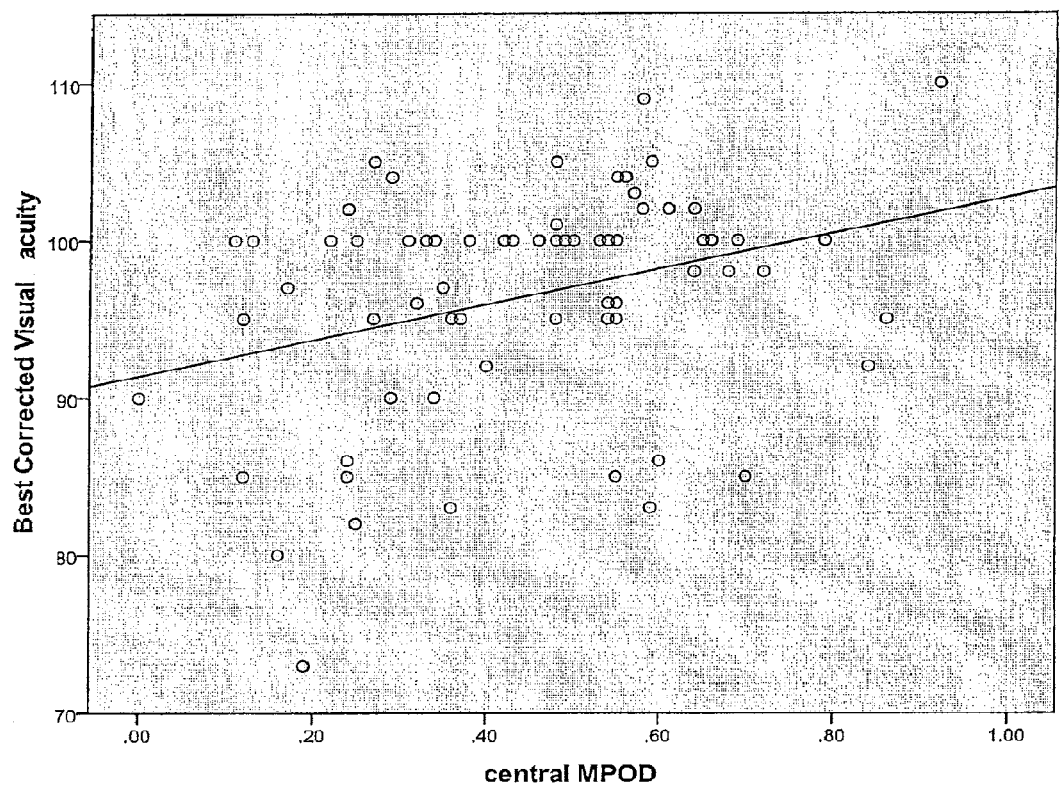
FIG. 2 is a graph of corrected visual acuity against central macular pigment OD (arbitrary units) in a group of mixed normal and AMD subjects.

There was a positive and statistically significant relationship between central MPOD (at 0.25°) and corrected visual acuity at baseline (r=0.303, p=0.008), as shown in FIG. 2 which is a graph of corrected visual acuity against MPOD (arbitrary units), showing the data points for individual subjects in the two groups prior to supplementation with one of the three carotenoid formulations. This finding suggests that central MP is significantly and positively related to visual performance.

Increase in MPOD Over Time

Figure 3:
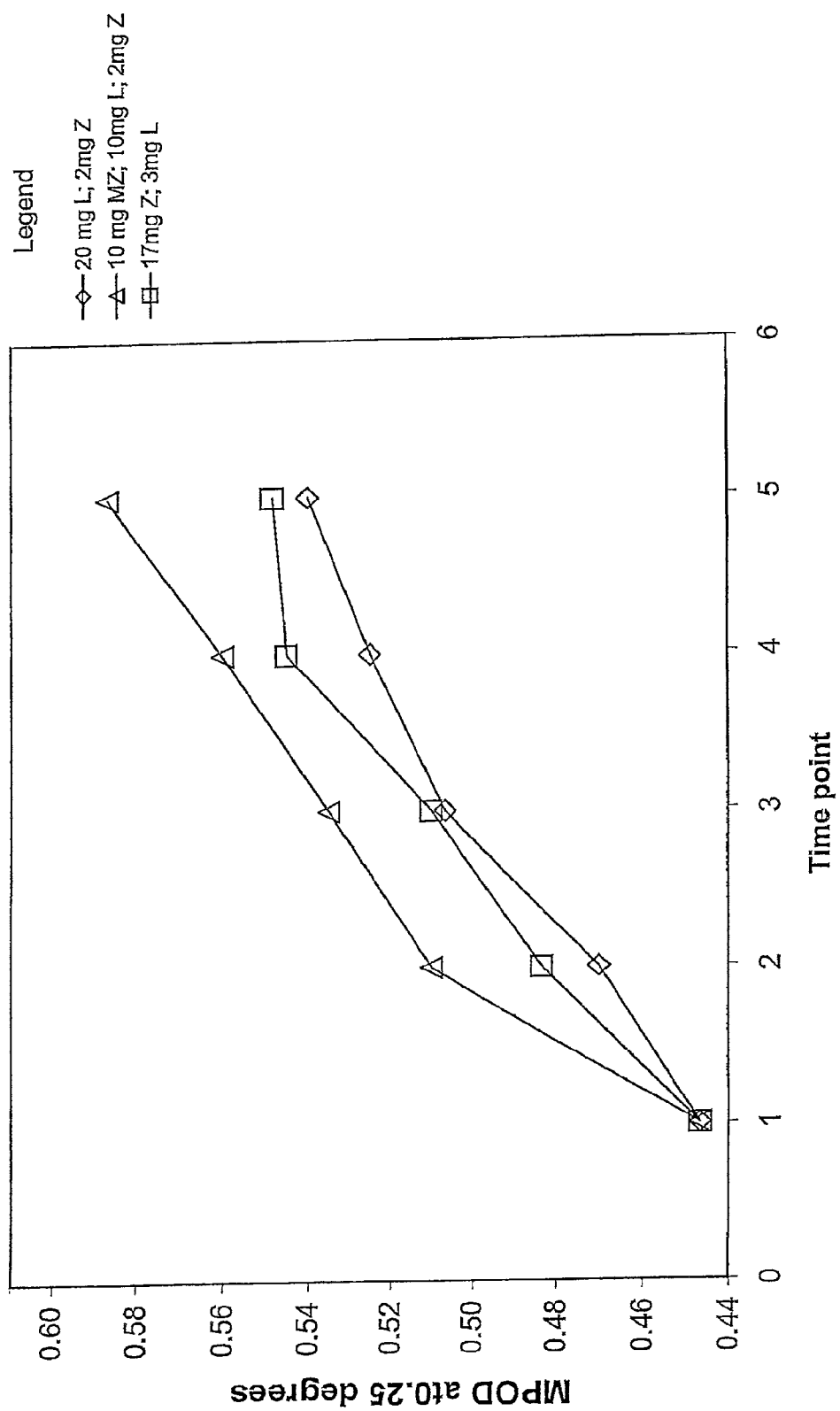
FIG. 3 is a graph of macular pigment OD (at 0.25° eccentricity) against time for subjects consuming various macular carotenoid compositions.

At an eccentricity of 0.25° the baseline MPOD was different for each group as follows; Group 1: 0.42±0.20 Group 2:0.44±0.18 Group3: 0.49±0.21, with a mean of all groups of 0.45±0.20. To simplify the comparison all groups are drawn to start at the mean value. The study showed an increase in MPOD over time, as illustrated in FIG. 3, which is a graph of MPOD at 0.25° eccentricity (arbitrary units) against time (timepoints 1 to 5, corresponding to 0, 2, 4, 6 & 8 weeks respectively). As seen in FIG. 3, the biggest increase in central MPOD was achieved with the group 2 formulation (MZ=10 mg/day, L=10 mg/day, Z=2 mg/day) which was statistically significant different from groups 1 and 3. There was no statistical difference between group 1 and 3.

Conclusions

Surprisingly, the greatest effect on macular pigment was seen with the mixed carotenoid group (group 2) containing MZ10 mg L10 mg Z 2 mg, whereas results with the other two groups were very similar. There appears to be synergism between MZ & L. That the high MZ group (group 3) was able to increase MP demonstrates that MZ can raise MPOD substantially without any contribution from the other carotenoids, but was less effective than MZ in combination with L.

Macular Carotenoid Supplementation in Subjects with 'Central Dips' in their Macular Pigment Spatial Profiles The central retina, known as the macula, is responsible for color and fine-detail vision (Hirsh & Curcio 1989; Vision Res. 29, 1095-1101). A pigment of the two dietary carotenoids, lutein (L) and zeaxanthin (Z), and a typically non-dietary carotenoid MZ (MZ), (Johnson et al., 2005 Invest. Ophtalmol. Vis. Sci. 46, 692-702) accumulates at the macula, where it is known as macular pigment (MP). MP is a blue light filter (Snodderly et al., 1984 Invest. Opthalmol. Vis. Sci. 25, 660-673) and a powerful antioxidant (Khachik et al. 1997 Invest. Ophthalm. & Vis. Sci. 38, 1802-1811), and is therefore believed to protect against age-related macular degeneration (AMD), which is now the most common cause of blind registration in the western world (Klaver et al., 1998 Arch. Ophthalmol. 116, 653-658).

MZ and Z are the predominant carotenoids in the foveal region, whereas L predominates in the parafoveal region (Snodderley et al., 1991 Invest. Ophthalmol. Vis. Sci. 32, 268-279). The concentration of MZ peaks centrally, with an MZ:Z ratio of 0.82 in the central retina (within 3 mm of the fovea) and 0.25 in the peripheral retina (11-21 mm from the fovea) (Bone et al., 1997 Experimental Eye Research 64, 211-218). Retinal MZ is produced primarily by isomerization of retinal L, thus accounting for lower relative levels of L, and higher relative levels of MZ, in the central macula, and vice versa in the peripheral macula, and would also explain why MZ accounts for about one third of total MP.

The concentration of MP varies greatly amongst individuals (Hammond et al., 1997 Journal of the Optical Society of America A-Optics Image Science & Vision, 14, 1187-1196). Atypical MP spatial profiles (i.e. 'central dips') are present in some individual MP profiles. More importantly, it was confirmed that these 'central dips' were real and reproducible features of the MP spatial profile, when measured using customised heterochromatic flicker photometry (cHFP, a validated technique for measuring MP). The importance of such variations, if any, in the spatial profile of MP (e.g. the presence of a 'central dip') is not yet known, but may be related to the putative protective role of this pigment. For example, reduced MPOD at the centre of the macula (i.e. the presence of a 'central dip') may be associated with increased risk of developing AMD.

It has been shown that 12% (58 subjects out of a sample database of 484 subjects) of the normal Irish population had a reproducible 'central dip' in their MPOD spatial profile and that such a dip in the MP spatial profile is more common in older subjects and in cigarette smokers (two of the established risk factors for AMD).

EXAMPLE 2

Figure 4:
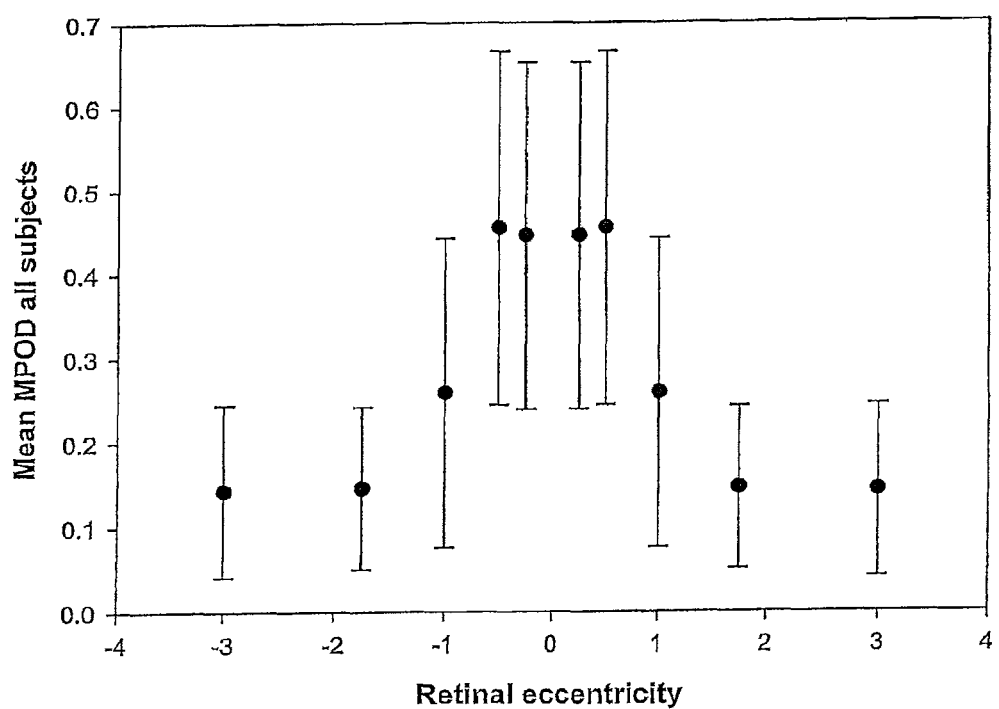
FIG. 4 is a graph showing the macular pigment OD measurement, at varying degrees of eccentricity, for particular subjects found to have atypical MPOD profiles, with a "central dip" (i.e. lower levels of macular pigment in the centre of the macula); mean±SD MPOD values showing the 'central dip' in the spatial profile of MP. Temporal MPOD values were measured at 0.25°, 0.5°, 1°, 1.75°, 3° of eccentricity. Specifically, given the known symmetry of MPOD, the MPOD values for negative eccentricities were assumed to be the same and constructed for the purpose of illustration.

Supplementation of Formulations Containing Macular Carotenoids to Subjects with a "Central Dip" in their MP Profile The study described in this example was performed with volunteer subjects from the above mentioned database (n=58) in the "central dip study", who were identified, and confirmed, as having 'central dips' in their MP spatial profile (i.e. MPOD at 0.5 degrees of eccentricity was ≥MPOD at 0.25 degrees of eccentricity, see FIG. 4) and invited to participate in an 8-week supplementation trial with one of three different macular carotenoid formulations (see below).

Methods

Subjects and Study Design:

Fifty eight subjects with 'central dips' in their MP spatial profile (identified from a master MP database; n=484) were invited to take part in the study. Of the 40 subjects that agreed to come back for testing, 31 were confirmed as still having a 'central dip' (i.e. MPOD at 0.5 degrees of eccentricity was ≥MPOD at 0.25 degrees of eccentricity) and were therefore enrolled into the 8-week supplementation trial.

All subjects signed an informed consent document and the experimental measures conformed to the Declaration of Helsinki. The study was reviewed and approved by the Research Ethics Committee, Waterford Institute of Technology, Waterford, Ireland. Inclusion criteria for participation in this study were as follows: MPOD at 0.5 degrees of eccentricity ≥MPOD at 0.25 degrees of eccentricity (i.e. evidence of a 'central dip' in the MP spatial profile); no presence of ocular pathology; visual acuity 20/60 or better in the study eye; not currently taking L and/or Z and/or MZ dietary supplements.

Subjects were randomly assigned into one of the three groups as follows;
Group 1: high L group (n=11), L=20 mg/day, Z=2 mg/day;
Group 2: mixed carotenoid group (n=10), MZ=10 mg/day, L=10 mg/day, Z=2 mg/day.
Group 3 the high MZ group (n=10), 18 mg/day MZ, 2 mg/day L).

All subjects were instructed to take one capsule per day with a meal for 8 weeks. MPOD, including its spatial profile, i.e. at 0.25°, 0.5°, 1°, 1.75°, 3°, was measured at baseline, four weeks and 8 weeks.

Measurement of Macular Pigment Optical Density

The spatial profile of MP was measured using cHFP using the Macular Densitometer™, as described in Example 1. In order to measure the spatial profile of MP, measurements were made at the following degrees of retinal eccentricity: 0.25°, 0.5°, 1°, 1.75°, 3° and 7° (the reference point) obtained using the following sized target diameters; 30 minutes, 1°, 2°, 3.5°, 1° and 2°, Statistical Analysis The statistical software package PASW Statistics 17.0 (SPSS Inc., Chicago, Ill., USA) was used for analysis and Sigma Plot 8.0 (Systat Software Inc., Chicago, Ill., USA) was used for graphical presentations. All quantitative variables investigated exhibited a typical normal distribution. Means±SDs are presented in the text and tables. Statistical comparisons of the three different intervention groups, at baseline, were conducted using independent samples t-tests and chi-square analysis, as appropriate. We used the 5% level of significance throughout our analysis.

Results

Change in MPOD Over 8-Week Supplementation Period

Figure 5:
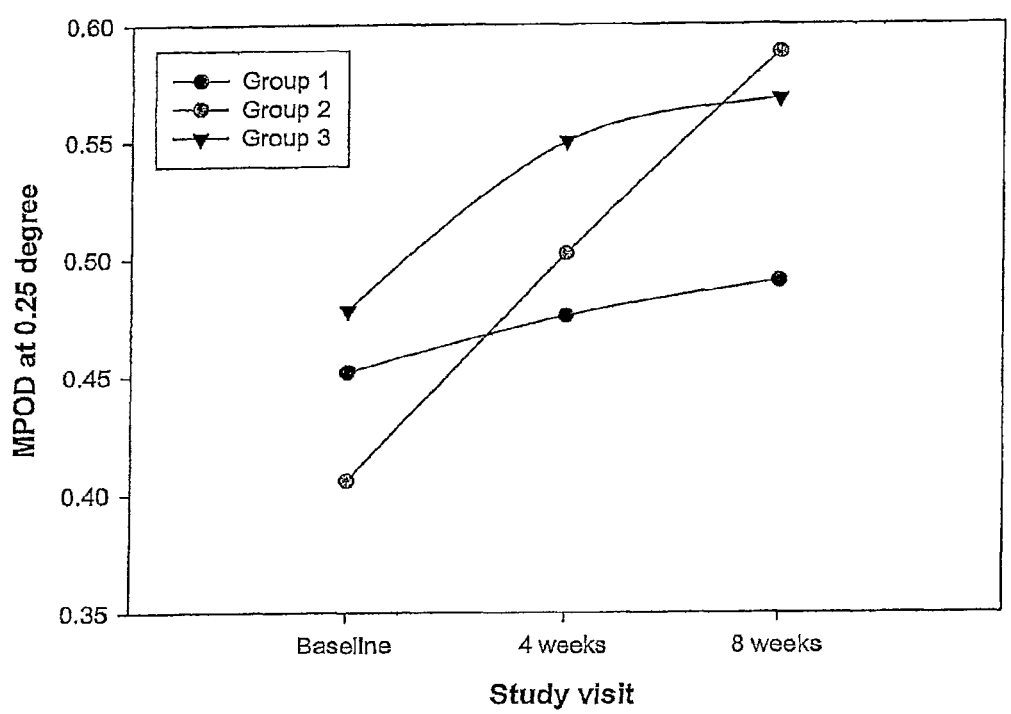
FIG. 5 is a graph of MPOD against time, for subjects receiving one of three different macular carotenoid formulations, wherein mean macular pigment optical density is measured at 0.25° retinal eccentricity at baseline, 4 weeks, and 8 weeks according to group wise; n=31; Group 1: high L group; Group 2: mixed carotenoid group; Group 3: high MZ group.
Figure 6:
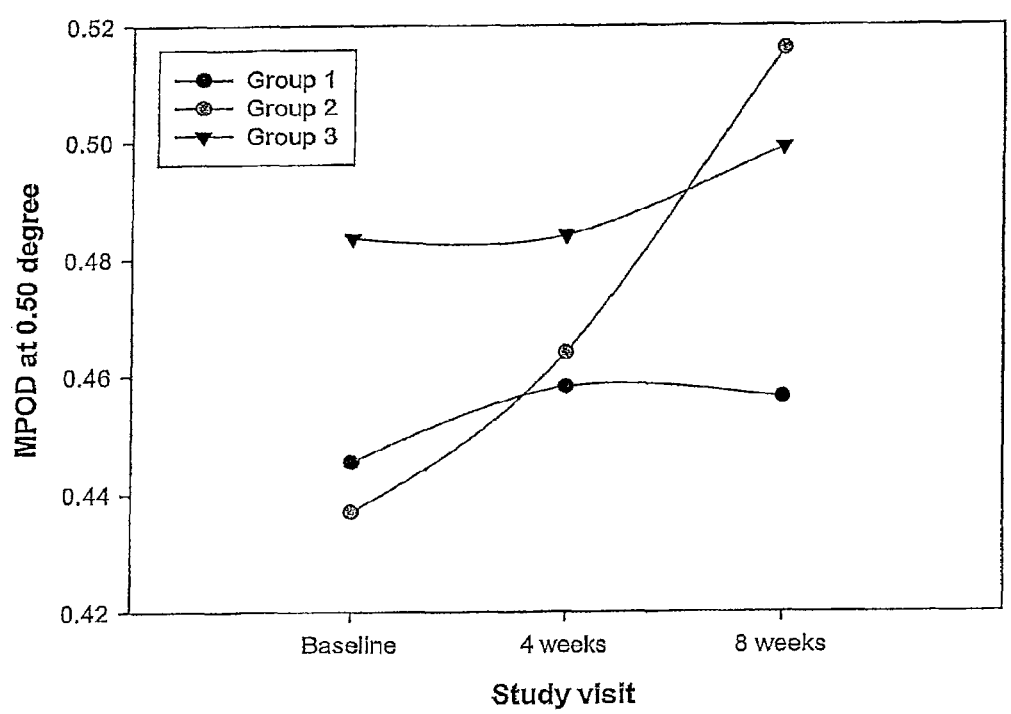
FIG. 6 is a graph of MPOD against time, for subjects receiving one of three different macular carotenoid formulations, wherein mean macular pigment optical density is measured at 0.50° retinal eccentricity at baseline, 4 weeks, and 8 weeks according to group wise; n=31; Group 1: high L group; Group 2: mixed carotenoid group; Group 3: high MZ group.

We conducted repeated measures ANOVA of MPOD, for all retinal eccentricities measured (i.e. at 0.25°, 0.5°, 1.0°, 1.75°, and 3°), over time (i.e. over the study period [baseline, 4 weeks and 8 weeks]), using a general linear model approach, with one between-subjects factor: treatment (Group 1, Group 2, Group 3) and age as a covariate. FIGS. 5 and 6 show the change in MPOD during the course of the trial for measurements at 0.25 and 0.5° eccentricity respectively. Table 1 presents repeated measures ANOVA results for each group separately and for each degree of retinal eccentricity. As seen in this Table, increase in MPOD at 0.25° and 0.5° was statistically significant in Group 2 (i.e. the mixed carotenoids group). Similarly, a significant increase in MPOD at 0.25° was seen in Group 3 (i.e. high MZ group). Of note, only the increase in MPOD at 0.25° in Group 2 remains significant after Bonferroni correction for multiple testing.

Figure 7:
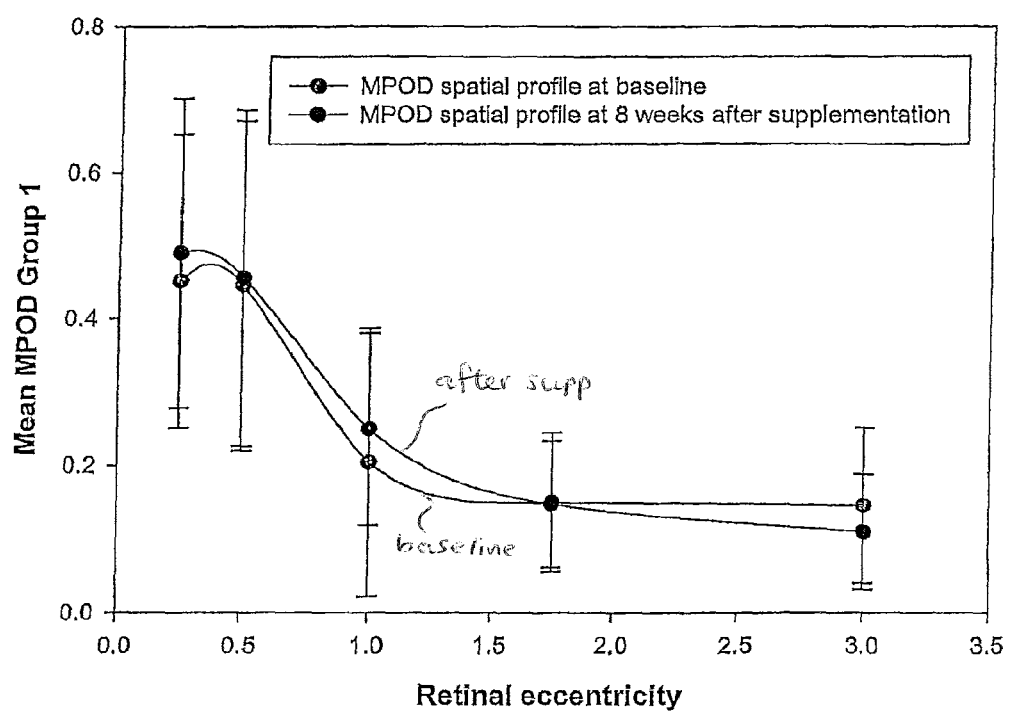
FIG. 7 is a graph of mean MPOD against retinal eccentricity for Group 1 respectively (see example 2), before and after an 8 week period of dietary supplementation, wherein the mean macular pigment optical density spatial profile of Group 1 is measured at baseline (pre supplementation) and at 8 weeks (post supplementation); mean±standard deviation; n=11; Group 1: high L group.
Figure 8:
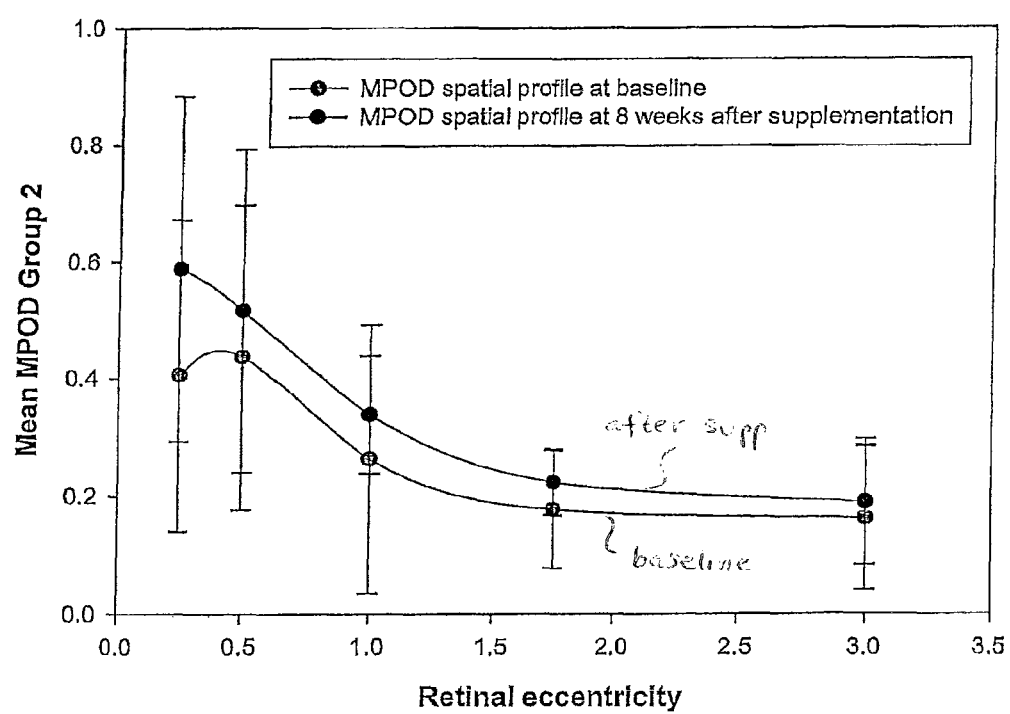
FIG. 8 is a graph of mean MPOD against retinal eccentricity for Group 2 (see example 2), before and after an 8 week period of dietary supplementation, wherein the mean macular pigment optical density spatial profile of Group 2 is measured at baseline (pre supplementation) and at 8 weeks (post supplementation); mean±standard deviation; n=10; Group 2: combined carotenoid group.
Figure 9:
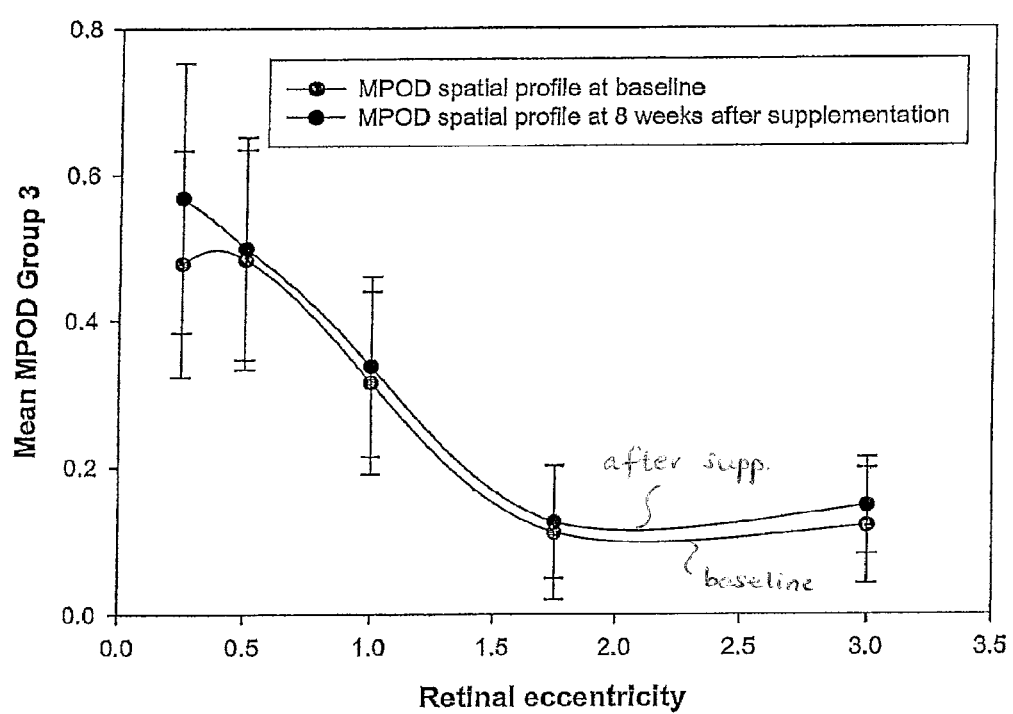
FIG. 9 is a graph of mean MPOD against retinal eccentricity for Group 3 (see example 2), before and after an 8 week period of dietary supplementation, wherein the mean macular pigment optical density spatial profile of Group 3 is measured at baseline (pre supplementation) and at 8 weeks (post supplementation); mean±standard deviation; n=10; Group 3: high MZ group.

Change in the spatial profile of MPOD for each of Groups 1-3 is illustrated in FIGS. 7-9 respectively.

Conclusions

Only the two formulations containing MZ were able to correct the "central dip" and increase MP. Surprisingly, and contrary to expectation, the formulation containing L but without MZ had no effect on MPOD at any eccentricity.

The formulation containing mixed carotenoids (group 2) had a superior effect since it increased MP significantly at both 0.25 and 0.5 eccentricities. This is consistent with the result from the subjects who received a supplement with all three carotenoids without a central dip at the baseline (see Example 1) i.e. the greatest response was observed using a supplement containing each of MZ, L and Z.

TABLE 1

Average MPOD values at each degree of eccentricity for all subjects according to group & visit wise

| Group | MPOD | Baseline | 4 wks | 8 wks | Time interaction (p-value) |
| --- | --- | --- | --- | --- | --- |
| Group 1 | 0.25 | 0.45 ± 0.20 | 0.48 ± 0.22 | 0.49 ± 0.21 | 0.112 |
| Group 1 | 0.5 | 0.45 ± 0.23 | 0.46 ± 0.18 | 0.46 ± 0.23 | 0.509 |
| Group 1 | 1 | 0.20 ± 0.18 | 0.27 ± 0.15 | 0.25 ± 0.13 | 0.234 |
| Group 1 | 1.75 | 0.15 ± 0.09 | 0.15 ± 0.09 | 0.15 ± 0.09 | 0.986 |
| Group 1 | 3 | 0.15 ± 0.11 | 0.16 ± 0.09 | 0.11 ± 0.08 | 0.265 |
| Group 2 | 0.25 | 0.41 ± 0.27 | 0.50 ± 0.27 | 0.59 ± 0.30 | 0.000 |
| Group 2 | 0.5 | 0.44 ± 0.26 | 0.46 ± 0.28 | 0.52 ± 0.28 | 0.016 |
| Group 2 | 1 | 0.26 ± 0.23 | 0.29 ± 0.15 | 0.34 ± 0.10 | 0.417 |
| Group 2 | 1.75 | 0.18 ± 0.10 | 0.19 ± 0.06 | 0.22 ± 0.06 | 0.218 |
| Group 2 | 3 | 0.16 ± 0.12 | 0.14 ± 0.06 | 0.19 ± 0.11 | 0.448 |
| Group 3 | 0.25 | 0.48 ± 0.16 | 0.55 ± 0.19 | 0.57 ± 0.18 | 0.005 |
| Group 3 | 0.5 | 0.48 ± 0.15 | 0.48 ± 0.17 | 0.50 ± 0.15 | 0.786 |
| Group 3 | 1 | 0.32 ± 0.12 | 0.31 ± 0.13 | 0.34 ± 0.12 | 0.596 |
| Group 3 | 1.75 | 0.11 ± 0.09 | 0.12 ± 0.07 | 0.13 ± 0.08 | 0.743 |
| Group 3 | 3 | 0.12 ± 0.08 | 0.15 ± 0.07 | 0.15 ± 0.07 | 0.522 |

Values represent mean ± standard deviation; n = 31; MPOD = macular pigment optical density; 0.25° = MPOD measured at 0.25° retinal eccentricity; 0.5° = MPOD measured at 0.5° retinal eccentricity; 1.0° = MPOD measured at 1.0° retinal eccentricity; 1.75° = MPOD measured at 1.75° retinal eccentricity; 3° = MPOD measured at 3.0° retinal eccentricity; Group 1: high L group; Group 2: combined carotenoid group; Group 3: high MZ group; the p-values represent repeated measures ANOVA for the 3 study visits (within-subject effects), with Greenhouse-Gesser correction for lack of sphericity as appropriate.

EXAMPLE 3

Comparison of Visual Performance in Subjects with Early Stage AMD after Supplementation with Three Different Macular Carotenoid Formulations Subjects and Recruitment This study was conducted with 72 subjects, many with early AMD. For details see Example 1.

Study Design and Formulation

The subjects with were divided into 3 groups (of 20-27 subjects) and given the following supplementations:
Group 1: L=20; Z=2 mg/day
Group 2: L=10; MZ=10; Z=2 mg/day
Group 3: MZ=17-18; L=2-3; Z=2 mg/day These formulations, dissolved in 0.3 ml vegetable oil, were administered in soft gel capsules.

Visual Performance, using the techniques described previously above, was measured at baseline and at 3 and 6 months after supplementation. Statistical analyses were performed using a paired t test. Significant values were considered as P<0.05. Results are only given where at least one group was statistically significant.

Results:

Since there were no statistically significant improvements detected in VP after 3 months treatment, only results for 6 or 12 months are presented here (below):

1. Baseline Comparison Between Groups:

TABLE 2

Baseline Comparison

| Variable | Group 1: 20 mg L; 2 mg Z | Group 2: 10 mg MZ; 10 mg L; 2 mg Z | Group 3: 18 mg MZ; 2 mg L | p |
| --- | --- | --- | --- | --- |
| N | 23 | 27 | 22 | |
| Age | 67 ± 8 | 64 ± 9 | 72 ± 10 | 0.014 |
| MPOD 0.25° | 0.412 ± 0.19 | 0.482 ± 0.21 | 0.475 ± 0.20 | 0.411 |
| BCVA | 92 ± 21 | 97 ± 10 | 94 ± 8 | 0.362 |

The groups were statistically comparable at baseline with respect to MP and vision (assessed by Best Corrected Visual Acuity, "BCVA"). There was a significant difference between groups at baseline for age between Group 3 and the other two Groups. Group 1 and Group 2 were statistically similar with respect to age.

2. Best Corrected Visual Acuity (BCVA)

There was a baseline correlation (before supplementation) of a positive and statistically significant relationship between central MPOD (0.25) and BCVA, importantly this is in the AMD population (r–0.368, p=0.002). There was no statistically significant change in BCVA in any group after 3 and 6 months.

A computer-generated LofMAR test chart (Test Chart 2000 Pro; Thomson Software Solutions) was used to determine BCVA at a viewing distance of 4 m, using a Sloan ETDRS letterset. BCVA was determined as the average of three measurements, with letter and line changes facilitated by the software pseudo-randomization feature. Best corrected visual acuity was recorded using a letter-scoring visual acuity rating, with 20/20 (6/6) visual acuity assigned a value of 100. Best corrected visual acuity was scored relative to this value, with each letter correctly identified assigned a nominal value of one, so that, for example, a BCVA of 20/20+1 (6/6+1) equated to a score of 101, and 20/20-1 (6/6-1) to 99.

3. MPOD Response

Table 3 below presents MP data for each Group and for each eccentricity measured, at baseline, six and twelve months after supplementation with macular carotenoids.

A statistically significant increase in MPOD at 12 months was observed only in groups 2 and 3, receiving the MZ-containing supplement.

TABLE 3

| Group | MPOD Baseline | MPOD 6 months | MPOD 12 months | |
|---|---|---|---|---|
| | 0.25 | 0.25 | | p |
| 1: | 0.42 ± 0.19 | 0.51 ± 0.20 | 0.57 ± 0.30 | 0.148 |
| 2: | 0.48 ± 0.22 | 0.58 ± 0.21 | 0.63 ± 0.19 | 0.001 |
| 3: | 0.52 ± 0.20 | 0.58 ± 0.22 | 0.57 ± 0.20 | 0.022 |
| | 0.5 | 0.5 | | p |
| 1: | 0.32 ± 0.19 | 0.42 ± 0.18 | 0.46 ± 0.27 | 0.126 |
| 2: | 0.39 ± 0.19 | 0.50 ± 0.18 | 0.52 ± 0.19 | 0.001 |
| 3: | 0.41 ± 0.19 | 0.46 ± 0.19 | 0.45 ± 0.20 | 0.034 |

TABLE 3-continued

| Group | MPOD Baseline | MPOD 6 months | MPOD 12 months | |
|---|---|---|---|---|
| | 1.0 | 1.0 | | p |
| 1: | 0.22 ± 0.11 | 0.31 ± 0.15 | 0.32 ± 0.17 | 0.213 |
| 2: | 0.25 ± 0.12 | 0.36 ± 0.17 | 0.37 ± 0.18 | 0.001 |
| 3: | 0.26 ± 0.15 | 0.32 ± 0.14 | 0.33 ± 0.16 | 0.025 |
| | 1.75 | 1.75 | | p |
| 1: | 0.13 ± 0.10 | 0.18 ± 0.11 | 0.20 ± 0.10 | 0.114 |
| 2: | 0.14 ± 0.10 | 0.22 ± 0.12 | 0.24 ± 0.11 | <0.001 |
| 3: | 0.13 ± 0.11 | 0.21 ± 0.12 | 0.19 ± 0.10 | 0.063 |

4. Letter Contrast Sensitivity (Thomson Chart)

Table 4A presents letter contrast sensitivity data at baseline and six months after supplementation with macular carotenoids Measurements were made at 1.2, 2.4, 6.0, and 9.6 cpd. There was a statistically significant improvement only in Group 2 (10 mg MZ; 10 mg L; 2 mg Z) at 1.2, 2.4 and 9.6 cpd and not at all in the other two groups. This shows a greatly superior effect in Group 2.

TABLE 4A

| Group | Letter contrast sensitivity Baseline | Letter contrast sensitivity Six months | |
|---|---|---|---|
| | 1.2 cpd | 1.2 cpd | P |
| 1: | 1.68 ± 0.34 | 1.75 ± 0.30 | 0.091 |
| 2: | 1.63 ± 0.24 | 1.80 ± 0.25 | 0.013 |
| 3: | 1.68 ± 0.37 | 1.63 ± 0.25 | 0.322 |
| | 2.4 cpd | 2.4 cpd | p |
| 1: | 1.60 ± 0.33 | 1.66 ± 0.34 | 0.17 |
| 2: | 1.59 ± 0.29 | 1.72 ± 0.33 | 0.049 |
| 3: | 1.61 ± 0.35 | 1.63 ± 0.32 | 0.6 |
| | 9.6 cpd | 9.6 cpd | p |
| 1: | 1.1 ± 0.36 | 1.04 ± 0.41 | 0.194 |
| 2: | 0.97 ± 0.32 | 1.11 ± 0.46 | 0.043 |
| 3: | 0.94 ± 0.37 | 0.95 ± 0.43 | 0.901 |

Table 4B shows the letter contrast sensitivity (CS) at baseline and 12 months, for each of five spatial frequencies (1.2-15.15 cpd).

TABLE 4B

Mean (±sd) letter contrast sensitivity (CS) values at baseline and at 12 months.

| | Group 1 | | | Group 2 | | | Group 3 | | |
|---|---|---|---|---|---|---|---|---|---|
| cpd | Baseline | 12 months | p | Baseline | 12 months | p | Baseline | 12 months | P |
| 1.2 | 1.74 ± 0.31 | 1.86 ± 0.30 | 0.033 | 1.69 ± 0.24 | 1.88 ± 0.28 | 0.004 | 1.73 ± 0.30 | 1.89 ± 0.27 | 0.041 |
| 2.4 | 1.65 ± 0.32 | 1.79 ± 0.38 | 0.013 | 1.66 ± 0.28 | 1.79 ± 0.31 | 0.004 | 1.60 ± 0.30 | 1.85 ± 0.29 | 0.002 |
| 6.0 | 1.37 ± 0.29 | 1.42 ± 0.40 | 0.194 | 1.30 ± 0.29 | 1.38 ± 0.33 | 0.053 | 1.19 ± 0.43 | 1.55 ± 0.27 | 0.002 |
| 9.6 | 1.11 ± 0.28 | 1.09 ± 0.34 | 0.775 | 1.00 ± 0.32 | 1.10 ± 0.40 | 0.034 | 0.91 ± 0.45 | 1.19 ± 0.40 | 0.012 |
| 15.15 | 0.73 ± 0.33 | 0.73 ± 0.39 | 0.933 | 0.64 ± 0.37 | 0.73 ± 0.49 | 0.148 | 0.57 ± 0.46 | 0.83 ± 0.36 | 0.014 |

Abbreviations: cpd = cycles per degree

At 12 months the results were similar to 6 months in that letter contrast sensitivity increased in all groups for large objects (1.2 and 2.4 cpd) but only in groups 2 and 3 with smaller objects (6.0-15.5 cpd).

tive integers indicate regression (improvement) along the AMD severity scale. Between baseline and 12 months, there was no statistically significant difference between treatment groups with respect to change in AMD severity (p=0.223, Pearson chi-square test).

TABLE 4E

Change in AMD grade (11-step scale) between baseline and 12 months.

| Group | n | −2 | −1 | 0 | +1 | +2 | Sig. |
|---|---|---|---|---|---|---|---|
| 1 | 16 | 1 (6%) | 1 (6%) | 10 (63%) | 3 (19%) | 1 (6%) | 0.223 |
| 2 | 23 | 1 (4%) | 2 (9%) | 14 (61%) | 4 (17%) | 2 (9%) | |
| 3 | 15 | 2 (13%) | 6 (40%) | 4 (27%) | 2 (13%) | 1 (7%) | |
| Total | 54 (100%) | 4 (7%) | 9 (17%) | 28 (52%) | 9 (17%) | 4 (7%) | |

Abbreviations: n = number of subjects; negative value indicates disease progression; a positive value indicates disease regression; 0 = no change in grade Table 4C reports the relationship between observed changes in MPOD (at 0.25° eccentricity) and observed changes in letter CS at 1.2 cpd. Of note, there were no statistically significant relationships between change in MP and change in letter CS, at any spatial frequency.

TABLE 4C

| Change in MPOD vs. change in letter CS | r | p |
|---|---|---|
| Group 1 | 0.262 | 0.294 |
| Group 2 | 0.258 | 0.235 |
| Group 3 | −0.043 | 0.875 |

Colour Fundus Photographs

Colour fundus photographs were taken at every study visit using a Zeiss VisuCam™ (Carl Zeiss Meditec AG, Jena, Germany) and were graded stereoscopically at the Ocular Epidemiology Reading Center at the University of Wisconsin, USA. Photographs were graded using a modified version of the Wisconsin Age-Related Maculopathy Grading System. Early AMD was defined as the presence of drusen and/or pigmentary changes in at least one eye, confirmed by an on-site ophthalmologist in collaboration with graders at the University of Wisconsin. Each fundus photograph was evaluated, lesion-by-lesion, to determine maximum drusen size, type, area, and retinal pigmentary abnormalities. Overall findings were reported on an 11-step AMD severity scale. A change of two or more steps along the severity scale was defined as being clinically significant. Graded photographs were obtained for baseline and 12 months visits.

At baseline, there was no significant difference between the groups with respect to AMD grade (p=0.679) [Table 4D].

TABLE 4D

AMD grading for entire groups and subgroups at baseline.

| Grade | Entire group (n = 72) | Group 1 (n = 23) | Group 2 (n = 27) | Group 3 (n = 22) | Sig. |
|---|---|---|---|---|---|
| 1-3 | 16 (22.2%) | 7 (30.4%) | 6 (22.2%) | 3 (13.6%) | 0.679 |
| 4-5 | 28 (38.9%) | 10 (43.5%) | 8 (29.6%) | 10 (45.5%) | |
| 6-7 | 19 (26.4%) | 5 (21.7%) | 8 (29.6%) | 6 (27.3%) | |
| 8-9 | 4 (5.6%) | — | 2 (7.4%) | 2 (9.1%) | |
| 10-11 | 5 (6.9%) | 1 (4.3%) | 3 (11.1%) | 1 (4.5%) | |

The changes in AMD grade between baseline and 12 months for each of the three groups are summarized in Table 4E. A change in the negative direction (i.e. −1, −2) indicates a progression along the AMD severity scale, whereas posi- Of note, table 4E shows that 86% of subjects exhibited no clinically significant change in the status of their AMD between baseline and 12 months, with 7% exhibiting deterioration and 7% exhibiting an improvement (note: a change in grade of two or more has been accepted as being clinically significant).

Discussion

The most interesting results were for letter contrast sensitivity. This test is only conducted in daylight and tests letters of different sizes. Results were at 6 months and 12 months were similar. There was no correlation between increase in MP and increase in this parameter indicating a neuro-physiological effects of macular carotenoids.

There was no significant change in AMD grade from baseline. Thus changes in contrast sensitivity were not related to effects on AMD pathology.

5. Contrast Sensitivity at Night (Assessed on the FACT Device)

Table 5 below presents log contrast sensitivity data assessed for night time, at baseline and six months after supplementation with macular carotenoids. Measurements were made at 1.5, 3.0, 6.0, 12 and 18 cpm. The statistically significant improvement in this measure of VP was present only in Group 2 at 1.5, 3.0, cpd and in Group 1 at 1.5 cpd showing a superior effect of group 2.

TABLE 5

| Group | Night time contrast sensitivity Baseline | Night time contrast sensitivity Six months | |
|---|---|---|---|
| | 1.5 cpd | 1.5 cpd | P |
| 1: | 1.53 ± 0.29 | 1.67 ± 0.26 | 0.124 |
| 2: | 1.51 ± 0.27 | 1.66 ± 0.3 | 0.028 |
| 3: | 1.44 ± 0.29 | 1.45 ± 0.34 | 0.911 |
| | 3.0 cpd | 3.0 cpd | p |
| 1: | 1.52 ± 0.25 | 1.8 ± 0.28 | 0.001 |
| 2: | 1.62 ± 0.34 | 1.75 ± 0.41 | 0.01 |
| 3: | 1.55 ± 0.40 | 1.6 ± 0.41 | 0.585 |

6. Contrast Sensitivity at Daytime (Assessed on the FACT Device)

Table 6 below presents log contrast sensitivity data assessed for day time at baseline and six months after supplementation with macular carotenoids. Measurements were made at 1.5, 3.0. 6.0, 12 and 18 cpm. The statistically significant improvement in this measure of VP was present in Group 2 at 1.5, 3.0, and 18 cpd and in Group 1 at 1.5 cpd showing a superior effect in group 2.

TABLE 6

| Group | Daytime contrast sensitivity Baseline | Daytime contrast sensitivity Six months | |
|---|---|---|---|
| | 1.5 cpd | 1.5 cpd | P |
| 1: | 1.41 ± 0.16 | 1.57 ± 0.26 | 0.03 |
| 2: | 1.48 ± 0.23 | 1.6 ± 0.28 | 0.034 |
| 3: | 1.41 ± 0.13 | 1.5 ± 0.28 | 0.238 |
| | 3.0 cpd | 3.0 cpd | p |
| 1: | 1.67 ± 0.21 | 1.75 ± 0.21 | 0.17 |
| 2: | 1.7 ± 0.33 | 1.81 ± 0.34 | 0.018 |
| 3: | 1.72 ± 0.18 | 1.77 ± 0.29 | 0.46 |
| | 18 cpd | 18 cpd | p |
| 1: | 0.62 ± 0.4 | 0.56 ± 0.41 | 0.497 |
| 2: | 0.65 ± 0.38 | 0.77 ± 0.5 | 0.015 |
| 3: | 0.57 ± 0.4 | 0.62 ± 0.43 | 0.704 |

7. Contrast Sensitivity at Night Time in the Presence of Glare (Assessed on the FACT Device)

Table 7 below presents Log contrast sensitivity data at night in the presence of glare at baseline and six months after supplementation with macular carotenoids. Measurements were made at 1.5, 3.0, 6.0, 12 and 18 cpd. There was a statistically significant improvement in this VP only in Group 2 at 18 cpd.

TABLE 7

| Group | Night time contrast sensitivity with glare Baseline 18 cpd | Night time contrast sensitivity with glare Six months 18 cpd | p |
|---|---|---|---|
| 1: | 0.34 ± 0.16 | 0.34 ± 0.16 | 0.136 |
| 2: | 0.36 ± 0.13 | 0.47 ± 0.34 | 0.038 |
| 3: | 0.36 ± 0.22 | 0.32 ± 0.08 | 0.588 |

8. Contrast Sensitivity at Day Time in the Presence of Glare (Assessed on the FACT Device)

Table 8 below presents Log contrast sensitivity data at day time in the presence of glare, at baseline and six months after supplementation with macular carotenoids. Measurements were made at 1.5, 3.0, 6.0, 12 and 18 cpd. The statistically significant improvement in this measure of VP was present in Group 2 at 1.5, 3.0, 6.0, and 18 cpd cpd and in Group 1 at 1.5, 3.0, and 6.0 cpd and in Group 3 at 6 cpd, showing a superior effect in group 2.

TABLE 8

| Group | Daytime contrast sensitivity with glare Baseline | Daytime contrast sensitivity with glare Six months | |
|---|---|---|---|
| | 1.5 cpd | 1.5 cpd | P |
| 1: | 1.5 ± 0.25 | 1.63 ± 0.21 | 0.001 |
| 2: | 1.43 ± 0.25 | 1.68 ± 0.24 | 0.002 |
| 3: | 1.42 ± 0.38 | 1.46 ± 0.36 | 0.351 |

TABLE 8-continued

| Group | Daytime contrast sensitivity with glare Baseline | Daytime contrast sensitivity with glare Six months | |
|---|---|---|---|
| | 3.0 cpd | 3.0 cpd | p |
| 1: | 1.68 ± 0.22 | 1.85 ± 0.22 | 0.006 |
| 2: | 1.71 ± 0.25 | 1.84 ± 0.25 | 0.007 |
| 3: | 1.67 ± 0.35 | 1.71 ± 0.43 | 0.542 |
| | 6.0 cpd | 6.0 cpd | p |
| 1: | 1.46 ± 0.42 | 1.85 ± 0.22 | <0.001 |
| 2: | 1.46 ± 0.47 | 1.84 ± 0.25 | <0.001 |
| 3: | 1.36 ± 0.42 | 1.71 ± 0.43 | 0.001 |
| | 18 cpd | 18 cpd | p |
| 1: | 0.64 ± 0.46 | 0.59 ± 0.43 | 0.642 |
| 2: | 0.53 ± 0.32 | 0.67 ± 0.51 | 0.018 |
| 3: | 0.7 ± 0.47 | 0.66 ± 0.45 | 0.609 |

9. Contrast Sensitivity and Glare Disability Between Baseline and 12 Months

Data on contrast sensitivity (CS) and glare disability (GD) under mesopic (night-time) and photopic (daytime) conditions, at baseline and 12 months, are presented in Tables 9-12.

TABLE 9

Log CS at baseline and 12 months under mesopic conditions (FACT device)

| Group | | | p |
|---|---|---|---|
| | CS 1.5 cpd v1 | CS 1.5 cpd v4 | |
| Group 1 | 1.59 ± 0.28 | 1.80 ± 0.22 | 0.007 |
| Group 2 | 1.60 ± 0.27 | 1.76 ± 0.24 | 0.047 |
| Group 3 | 1.53 ± 0.39 | 1.73 ± 0.25 | 0.124 |
| | CS 3 cpd v1 | CS 3 cpd v4 | |
| Group 1 | 1.61 ± 0.25 | 1.82 ± 0.22 | 0.007 |
| Group 2 | 1.68 ± 0.34 | 1.80 ± 0.26 | 0.058 |
| Group 3 | 1.62 ± 0.42 | 1.85 ± 0.40 | 0.175 |
| | CS 6 cpd v1 | CS 6 cpd v4 | |
| Group 1 | 1.18 ± 0.38 | 1.24 ± 0.53 | 0.521 |
| Group 2 | 1.27 ± 0.40 | 1.38 ± 0.44 | 0.278 |
| Group 3 | 1.20 ± 0.44 | 1.46 ± 0.50 | 0.060 |
| | CS 12 cpd v1 | CS 12 cpd v4 | |
| Group 1 | 0.65 ± 0.14 | 0.79 ± 0.43 | 0.224 |
| Group 2 | 0.67 ± 0.26 | 0.79 ± 0.24 | 0.080 |
| Group 3 | 0.76 ± 0.25 | 0.89 ± 0.36 | 0.177 |

TABLE 9-continued

Log CS at baseline and 12 months under mesopic conditions (FACT device)

| Group | CS 18 cpd v1 | CS 18 cpd v4 | p |
|---|---|---|---|
| Group 1 | 0.40 ± 0.25 | 0.32 ± 0.08 | 0.207 |
| Group 2 | 0.32 ± 0.07 | 0.36 ± 0.26 | 0.332 |
| Group 3 | 0.36 ± 0.15 | 0.39 ± 0.24 | 0.476 |

Abbreviations:
FACT = functional acuity contrast test;
CS = contrast sensitivity;
cpd = cycles per degree;
v1 = baseline visit;
v4 = 12 month visit

TABLE 10

Log CS at baseline and 12 months under photopic conditions (FACT device)

| Group | CS 1.5 cpd v1 | CS 1.5 cpd v4 | p |
|---|---|---|---|
| Group 1 | 1.47 ± 0.25 | 1.63 ± 0.22 | 0.007 |
| Group 2 | 1.56 ± 0.21 | 1.61 ± 0.24 | 0.478 |
| Group 3 | 1.44 ± 0.22 | 1.63 ± 0.25 | 0.023 |

| Group | CS 3 cpd v1 | CS 3 cpd v4 | p |
|---|---|---|---|
| Group 1 | 1.70 ± 0.22 | 1.86 ± 0.11 | 0.002 |
| Group 2 | 1.74 ± 0.33 | 1.86 ± 0.21 | 0.108 |
| Group 3 | 1.78 ± 0.20 | 1.84 ± 0.24 | 0.402 |

| Group | CS 6 cpd v1 | CS 6 cpd v4 | p |
|---|---|---|---|
| Group 1 | 1.52 ± 0.30 | 1.59 ± 0.29 | 0.310 |
| Group 2 | 1.52 ± 0.39 | 1.66 ± 0.39 | 0.064 |
| Group 3 | 1.44 ± 0.45 | 1.62 ± 0.38 | 0.192 |

| Group | CS 12 cpd v1 | CS 12 cpd v4 | p |
|---|---|---|---|
| Group 1 | 1.01 ± 0.33 | 0.98 ± 0.35 | 0.709 |
| Group 2 | 1.02 ± 0.36 | 1.21 ± 0.48 | 0.118 |
| Group 3 | 0.99 ± 0.43 | 1.19 ± 0.48 | 0.164 |

| Group | CS 18 cpd v1 | CS 18 cpd v4 | p |
|---|---|---|---|
| Group 1 | 0.63 ± 0.39 | 0.54 ± 0.40 | 0.437 |
| Group 2 | 0.59 ± 0.38 | 0.64 ± 0.48 | 0.687 |
| Group 3 | 0.68 ± 0.48 | 0.76 ± 0.50 | 0.458 |

Abbreviations:
FACT = functional acuity contrast test;
GD = glare disability;
cpd = cycles per degree;
v1 = baseline visit;
v4 = 12 month visit

TABLE 11

Log GD at baseline and 12 months under mesopic conditions (FACT device)

| Group | GD 1.5 cpd v1 | GD 1.5 cpd v4 | p |
|---|---|---|---|
| Group 1 | 1.49 ± 0.37 | 1.52 ± 0.34 | 0.635 |
| Group 2 | 1.44 ± 0.39 | 1.53 ± 0.35 | 0.365 |
| Group 3 | 1.26 ± 0.44 | 1.53 ± 0.47 | 0.029 |

| Group | GD 3 cpd v1 | GD 3 cpd v4 | p |
|---|---|---|---|
| Group 1 | 1.57 ± 0.43 | 1.60 ± 0.32 | 0.728 |
| Group 2 | 1.51 ± 0.38 | 1.70 ± 0.35 | 0.010 |
| Group 3 | 1.39 ± 0.50 | 1.55 ± 0.49 | 0.346 |

| Group | GD 6 cpd v1 | GD 6 cpd v4 | p |
|---|---|---|---|
| Group 1 | 1.09 ± 0.37 | 1.04 ± 0.34 | 0.564 |
| Group 2 | 1.18 ± 0.35 | 1.24 ± 0.43 | 0.581 |
| Group 3 | 1.10 ± 0.40 | 1.20 ± 0.47 | 0.348 |

| Group | GD 12 cpd v1 | GD 12 cpd v4 | p |
|---|---|---|---|
| Group 1 | 0.66 ± 0.17 | 0.71 ± 0.18 | 0.343 |
| Group 2 | 0.66 ± 0.17 | 0.80 ± 0.43 | 0.100 |
| Group 3 | 0.77 ± 0.24 | 0.69 ± 0.22 | 0.115 |

| Group | GD 18 cpd v1 | GD 18 cpd v4 | p |
|---|---|---|---|
| Group 1 | 0.34 ± 0.16 | 0.30 ± 0.00 | 0.336 |
| Group 2 | 0.34 ± 0.10 | 0.39 ± 0.37 | 0.483 |
| Group 3 | 0.32 ± 0.08 | 0.36 ± 0.21 | 0.336 |

Abbreviations:
FACT = functional acuity contrast test;
GD = glare disability;
cpd = cycles per degree;
v1 = baseline visit;
v4 = 12 month visit

TABLE 12

Log GD at baseline and 12 months under photopic conditions (FACT device)

| Group | GD 1.5 cpd v1 | GD 1.5 cpd v4 | p |
|---|---|---|---|
| Group 1 | 1.60 ± 0.25 | 1.76 ± 0.23 | 0.006 |
| Group 2 | 1.53 ± 0.19 | 1.74 ± 0.22 | 0.002 |
| Group 3 | 1.51 ± 0.25 | 1.69 ± 0.42 | 0.058 |

| Group | GD 3 cpd v1 | GD 3 cpd v4 | p |
|---|---|---|---|
| Group 1 | 1.70 ± 0.26 | 1.89 ± 0.25 | 0.002 |
| Group 2 | 1.78 ± 0.21 | 1.97 ± 0.18 | 0.001 |
| Group 3 | 1.73 ± 0.20 | 1.84 ± 0.38 | 0.330 |

| Group | GD 6 cpd v1 | GD 6 cpd v4 | p |
|---|---|---|---|
| Group 1 | 1.54 ± 0.38 | 1.64 ± 0.35 | 0.358 |
| Group 2 | 1.56 ± 0.43 | 1.69 ± 0.34 | 0.087 |
| Group 3 | 1.46 ± 0.47 | 1.71 ± 0.38 | 0.048 |

| Group | GD 12 cpd v1 | GD 12 cpd v4 | p |
|---|---|---|---|
| Group 1 | 1.02 ± 0.42 | 1.05 ± 0.38 | 0.659 |
| Group 2 | 0.97 ± 0.36 | 1.14 ± 0.35 | 0.169 |
| Group 3 | 1.00 ± 0.44 | 1.11 ± 0.43 | 0.320 |

| Group | GD 18 cpd v1 | GD 18 cpd v4 | p |
|---|---|---|---|
| Group 1 | 0.64 ± 0.45 | 0.67 ± 0.48 | 0.752 |
| Group 2 | 0.54 ± 0.34 | 0.81 ± 0.51 | 0.071 |
| Group 3 | 0.75 ± 0.48 | 0.75 ± 0.52 | 0.993 |

Abbreviations:
FACT = functional acuity contrast test;
GD = glare disability;
cpd = cycles per degree;
v1 = baseline visit;
v4 = 12 month visit Discussion Results at 12 months were similar to those at 6 months, in that the results were variable and difficult to interpret. Under mesopic (nighttime) conditions, contrast sensitivity only increased with large objects (1.5 and 3.0 cpd) in groups 1 and 2. For glare disability, group 1 did not change, whilst group 2 and 3 showed some change with large objects.

Under photopic (daylight) conditions, groups 1 and 3 only increased contrast sensitivity with large objects. With glare disability all groups increased only with large objects.

10. Changes in Visual Performance Parameters and Changes in MPOD

Table 13 reports the relationship between observed changes in MPOD (at 0.25° eccentricity) and observed changes in parameters of visual performance, namely CDVA and measures of mesopic and photopic contrast sensitivity, and mesopic and photopic glare disability, at 1.5 cpd. Of note, there were no statistically significant relationships between change in MP and change in visual performance in any of the groups (with the exception of a negative relationship between increases in MPOD and photopic CS at 1.5 cpd in Group 1 only).

TABLE 13

|  | r | p |
|---|---|---|
| Change in MPOD vs. change in CDVA | | |
| Group 1 | −0.320 | 0.211 |
| Group 2 | −0.148 | 0.558 |
| Group 3 | −0.126 | 0.681 |
| Change in MPOD vs. change in mesopic CS 1.5 cpd | | |
| Group 1 | 0.055 | 0.859 |
| Group 2 | −0.140 | 0.664 |
| Group 3 | 0.041 | 0.906 |
| Change in MPOD vs. change in photopic CS 1.5 cpd | | |
| Group 1 | −0.705 | 0.007 |
| Group 2 | −0.106 | 0.743 |
| Group 3 | −0.122 | 0.720 |
| Change in MPOD vs. change in mesopic GD 1.5 cpd | | |
| Group 1 | 0.318 | 0.289 |
| Group 2 | −0.106 | 0.743 |
| Group 3 | 0.388 | 0.238 |
| Change in MPOD vs. change in photopic GD 1.5 cpd | | |
| Group 1 | −0.262 | 0.388 |
| Group 2 | −0.136 | 0.673 |
| Group 3 | −0.308 | 0.357 |

Abbreviations: MPOD = macular pigment optical density; CDVA = corrected distance visual acuity; L = lutein; Z = zeaxanthin; MZ = meso-zeaxanthin; CS = contrast sensitivity; cpd = cycles per degree; GD = glare disability.

Discussion

There was no correlation between increases in visual performance and increases in macular pigment, indicating a neuro-physiological effect of macular carotenoids.

Other Conclusions: Changes in VP were Only Statistically Significant after 6 Months or More The methods reported here in contrast sensitivity were at varying spatial frequencies. Low spatial frequencies (e.g. 1.2 cpd) are indicative of very large objects (e.g. a car, a house), whereas, large spatial frequencies (e.g. 18 cpd) are indicative of small objects (e.g. a menu in a restaurant). The data lead to the following conclusions;

1. The most important effect was on contrast sensitivity which is one of the most important measures of VP and it reflects how the patient actually perceives their own vision.
2. Statistical significance was reached across many spatial frequencies, which means the improvement detected has implications for general and real life vision.
3. There was a superior improvement in VP for the Group 2 intervention (i.e. 10 mg MZ; 10 mg L; 2 mg Z).

EXAMPLE 4

Effect of Two Macular Carotenoids and a Placebo Formulations on VP in Normal Subjects Subjects and Recruitment This study was conducted on 36 normal subjects with no AMD. Details of the recruitment are given in Example 1. Of the 36 subjects recruited, 32 completed the trial, with one drop-out from each of the intervention groups and two drop-outs from group 3, the placebo group. All further analysis was confined to those subjects with a complete data set (Group 1, n=11; Group 2, n=11; Group 3, n=10).

Study Design and Formulations

The normal subjects were divided into 3 groups of (initially) 12 subjects and given the following supplements:
Group 1: L20; Z 2 mg/day
Group 2: MZ 10; L 10; Z 2 mg/day
Group 3: Placebo 0 mg/day The carotenoid formulations were in 0.3 ml vegetable oil and were administered in soft gel capsules.

Visual performance was assessed as described in detail below, at baseline, 3 months and at 6 months.

Statistical Analysis

The statistical software package PASW Statistics 18.0 (SPSS Inc., Chicago, Ill., USA) was used for analysis. All quantitative variables investigated exhibited a typical normal distribution. Means±SDs are presented in the text and tables. Statistical comparisons of the three supplementation groups, at baseline, were conducted using one way ANOVA, while paired samples t tests and repeated measures ANOVA (using a general linear model approach) were used to analyze visual performance and MPOD measures in each supplementation group for change across study visits as appropriate. Where relevant, the Greenhouse-Geisser correction for violation of sphericity was used. A 5% level of significance was used throughout the analysis.

Results

1. Baseline Analysis

Following randomization, one-way analysis of variance revealed no significant differences between groups at baseline, in terms of demographic, macular pigment, visual performance parameters, or other parameters, as illustrated for selected parameters in table 14 below.

TABLE 14

| Variable | Group 1: Mean ± SD | Group 2: Mean ± SD | Group 3: Placebo | P value |
|---|---|---|---|---|
| N | 12 | 12 | 12 | |
| Age | 56 ± 8 | 51 ± 13 | 46 ± 20 | 0.3 |
| BMI | 27 ± 3 | 25 ± 3 | 26 ± 5 | 0.31 |
| BCVA | 107 ± 5 | 109 ± 6 | 108 ± 6 | 0.72 |
| MPOD 0.25 | 0.32 ± 0.13 | 0.37 ± 0.13 | 0.35 ± 0.18 | 0.69 |
| MPOD 0.5 | 0.25 ± 0.14 | 0.27 ± 0.12 | 0.28 ± 0.16 | 0.88 |
| MPOD 1.0 | 0.15 ± 0.14 | 0.20 ± 0.07 | 0.16 ± 0.11 | 0.46 |
| MPOD 1.75 | 0.07 ± 0.10 | 0.10 ± 0.07 | 0.04 ± 0.04 | 0.16 |
| MPOD 3 | 0.07 ± 0.08 | 0.08 ± 0.07 | 0.04 ± 0.05 | 0.26 |

SD = standard deviation;
BMI = body mass index;
BCVA = best corrected visual acuity;
MPOD = macular pigment optical density

2. MPOD Response at 3 and 6 Months
MPOD Measurement

A spatial profile of MPOD was generated across 0.25°, 0.5°, 1°, 1.75° and 3° of retinal eccentricity in relation to a 7° reference location, using the Macular Densitometer™, which employs a heterochromatic flicker photometry (HFP) technique. Subjects were shown an explanatory video of the technique, and afforded a practice session prior to test commencement. HFP flicker frequencies were optimized following determination of individual critical flicker fusion (CFF) frequency measurements, in a customization process that optimizes MP measurements, (Stringham et al, Exp. Eye res. 2008, 87, 445-453). The MPOD measurement comprised the average of six readings (computed as the radiance value at which the subject reported null flicker) at each retinal eccentricity, and was deemed reliable and acceptable only when the standard deviation of null flicker responses was below 0.1

Contrast sensitivity was measured using a functional acuity contrast test (Optec6500 Vision Tester; Stereo Optical Co. Inc, Chicago, Ill.), which incorporates sine wave gratings, presented as Gabor patches, at spatial frequencies of 1.5, 3, 6, 12 and 18 cycles per degree (cpd) to produce a contrast sensitivity function. Testing was performed under mesopic (3 candelas per square meter [$cd/m^2$]) and photopic (85 cd/m2) conditions. (By way of explanation, 3 candelas per square meter is considered to represent the upper limit of mesopic conditions: any greater level of illumination is considered to constitute photopic conditions). Contrast sensitivity testing was performed using a Thomson Chart or using the EDTRS (Early Treatment Diabetic Retinopathy Study) letters in log MAR form at five different spatial frequencies (see Lorente-Velazquez et al., 2011 Optom. Vis Sci. 88 (10): 1245-1251).

Glare disability was assessed using the same test, and testing conditions, but in the presence of an inbuilt circumferential LED glare source (42 lux for mesopic and 84 lux for photopic glare testing). The LED glare source rendered

TABLE 15

MPOD response and significance at each retinal eccentricity across study visits

| Group Intervention | Baseline | 3 months | T test | 6 months | T Test | RM ANOVA |
|---|---|---|---|---|---|---|
| | MPOD0.25 | MPOD0.25 | p* | MPOD0.25 | p** | p*** |
| 20 mg L; 2 mg Z | 0.32 ± 0.12 | 0.38 ± 0.15 | 0.080 | 0.41 ± 0.14 | 0.444 | 0.092 |
| 10 mg MZ; 10 mg L; 2 mg Z | 0.37 ± 0.13 | 0.49 ± 0.14 | 0.002 | 0.50 ± 0.20 | 0.012 | 0.002 |
| Placebo | 0.35 ± 0.20 | 0.38 ± 0.20 | 0.709 | 0.37 ± 0.18 | 0.637 | 0.814 |
| | MPOD0.50 | MPOD0.50 | p | MPOD0.50 | P | p |
| 20 mg L; 2 mg Z | 0.27 ± 0.13 | 0.32 ± 0.22 | 0.456 | 0.30 ± 0.14 | 0.459 | 0.096 |
| 10 mg MZ; 10 mg L; 2 mg Z | 0.28 ± 0.12 | 0.38 ± 0.16 | 0.011 | 0.37 ± 0.21 | 0.042 | 0.010 |
| Placebo | 0.28 ± 0.17 | 0.31 ± 0.16 | 0.404 | 0.28 ± 0.16 | 0.966 | 0.572 |
| | MPOD1.0 | MPOD1.0 | p | MPOD1.0 | P | p |
| 20 mg L; 2 mg Z | 0.16 ± 0.14 | 0.18 ± 0.12 | 0.455 | 0.15 ± 0.14 | 0.767 | 0.533 |
| 10 mg MZ; 10 mg L; 2 mg Z | 0.21 ± 0.08 | 0.28 ± 0.10 | 0.035 | 0.27 ± 0.14 | 0.085 | 0.047 |
| Placebo | 0.16 ± 0.12 | 0.14 ± 0.11 | 0.954 | 0.13 ± 0.10 | 0.400 | 0.997 |
| | MPOD1.75 | MPOD1.75 | p | MPOD1.75 | P | p |
| 20 mg L; 2 mg Z | 0.08 ± 0.10 | 0.08 ± 0.10 | 0.859 | 0.07 ± 0.10 | 0.867 | 0.929 |
| 10 mg MZ; 10 mg L; 2 mg Z | 0.11 ± 0.07 | 0.19 ± 0.05 | 0.005 | 0.18 ± 0.10 | 0.041 | 0.036 |
| Placebo | 0.03 ± 0.03 | 0.03 ± 0.05 | 0.767 | 0.03 ± 0.05 | 0.732 | 0.815 |
| | MPOD3.0 | MPOD3.0 | p | MPOD3.0 | P | p |
| 20 mg L; 2 mg Z | 0.05 ± 0.02 | 0.07 ± 0.06 | 0.588 | 0.03 ± 0.03 | 0.185 | 0.671 |
| 10 mg MZ; 10 mg L; 2 mg Z | 0.09 ± 0.07 | 0.11 ± 0.11 | 0.275 | 0.10 ± 0.07 | 0.707 | 0.915 |
| Placebo | 0.02 ± 0.03 | 0.02 ± 0.03 | 0.810 | 0.02 ± 0.05 | 0.682 | 0.480 |

*difference between baseline and 3 months (paired samples t test)
**difference between baseline and 6 months (paired samples t test)
***repeated measures ANOVA across all visits It can be seen here that the greatest increase in MP, at all eccentricities measured, can be seen in Group 2, a supplement containing 10 mg MZ; 10 mg L; 2 mg Z.

Visual Performance Assessment

Visual acuity (VA) was measured at baseline with a computer-generated log MAR test chart (Test Chart 2000 Pro; Thompson Software Solutions, Hatfield, UK) at a viewing distance of 4 m, using the Sloan ETDRS letterset. VA was measured using a single letter scoring visual acuity rating, and recorded as the average of three measurements facilitated by the software letter randomization feature. The eye with better visual acuity was chosen as the study eye; however, when both eyes had the same corrected acuity, the right eye was chosen as the study eye.

a daylight simulating color temperature of 6500° K, and a spectral emission profile with a single large peak at 453 nm (close to peak MP spectral absorbance). These tests have been described in more detail elsewhere (Loughman et al. Vis Res. 2010; 50:1249-1256; Nolan et al. Vis Res. 2011; 51:459-69). The subject task, and nature of the test were explained in detail prior to test commencement, and subject performance was monitored closely by a trained examiner during the test, and reinstructed if necessary. Pupil diameter was measured for the background mesopic and photopic conditions used, and also in the presence of both glare sources using a Neuroptics VIP™-200 pupillometer (Neuroptics Inc., Irvine, Calif. 92612, USA).

automated photostress (MAP) test, an adaptation of the Humphrey visual field analyzer (Model 745i Carl Zeiss Meditec Inc. Dublin, Calif., USA) for the assessment of foveal incremental light threshold (Dhalla et al., Am J Ophthalmol. 2007; 143(4), 596-600). To isolate SWS cones, mid and long wavelength sensitive cones were desensitized using a three minute sustained exposure to a 100 cd/m$^2$, 570 nm bleaching background. A Goldmann V, 440 nm stimulus, presented for 200 milliseconds, was used to test the sensitivity of the SWS system before and after photostress. Following the three minute adaptation and practice session (during which subject performance was assessed for reliability and understanding), subjects were directed to fixate centrally between four circumferential light stimuli, and to respond to the detection of a "blue" stimulus at that location using the response button provided. Foveal sensitivity was determined as the average of three consecutive measurements recorded in decibels (dB), with each dB representing a 0.1 log unit sensitivity variation. Following baseline foveal sensitivity calculation, the subject was exposed to a short wavelength dominated photostress stimulus, which consisted of a 5-s exposure to a 300-W lamp viewed at 1 m through a low-pass glass dichroic filter, thus creating a temporary foveal "blue" after-image to mask fixation and reduce foveal sensitivity Immediately post-photostress, a continuous and timed cycle of foveal sensitivity measurements were conducted and recorded. The reduction in foveal sensitivity from baseline, along with the recovery characteristics of the SWS system sensitivity, was recorded. Pupil diameter was again recorded for background light conditions, and in the presence of the photostress light source.

Ocular straylight was measured using an Oculus C-Quant (OCULUS Optikgerate GmbH, Wetzlar, Germany), an instrument designed to quantify the effect of light scatter on vision. A central bipartite 14° test field was viewed monocularly through the instrument eyepiece. Subjects were instructed to respond, using the appropriate response button, to indicate the position of the most strongly flickering right or left test hemi-field. Subjects were allowed a defined practice session, during which reliable understanding of the task was assessed by the trained examiner Test results were deemed acceptable only when the standard deviation of measured straylight value (esd) was ≤0.08, and the reliability coefficient (Q) was ≥1. Absolute straylight values were recorded in logarithmic form [log(s)].

Photostress recovery time (PRT) of the short wavelength sensitive (SWS) visual system was assessed using a macular Visual discomfort was assessed during the glare disability and photostress testing procedures. Subjects were asked to rate their discomfort immediately following presentation of the glare and photostress light sources on a scale ranging from 1-10, where "1" indicated "no ocular discomfort", "5" indicated "moderate ocular discomfort", and "10" indicated "unbearable ocular discomfort". Such a scale has previously been used effectively in an exemplar macular pigment/glare study (Stringham et al., Invest Ophthalmol Vis Sci. 2011; 52(10):7406-15). Visual experience was also assessed by questionnaire, using a modified version of the Visual Activities Questionnaire, as used and described in detail elsewhere (Loughman et al. Vis Res. 2010; 50:1249-1256; Sloane et al., The Visual Activities Questionnaire: Developing an instrument for assessing problems in everyday visual tasks. *Technical Digest, Noninvasive Assessment of the Visual System, Topical Meeting of the Optical Society of America*, January, 1992). Iris color was also graded using a standardized iris classification scheme as defined by Seddon et al. (*Invest Ophthalmol Vis Sci* 1990 (31),8:1592-1598).

3. BCVA demonstrated no significant effect for any of the intervention groups at 3 months. At 6 months, pair t-test analysis revealed a statistically significant improvement in BCVA compared to baseline for group 2 (p=0.008). Repeated measures ANOVA confirmed a significant change across the three study visits for group 2 (p=0.034).

4. Contrast Sensitivity

Mesopic and photopic contrast sensitivity improved from baseline values across a range of spatial frequencies at three months, and in particular, at six months. At three months, statistically significant improvements were noted at 1.5 cpd (p=0.008) for mesopic conditions, and at 3 cpd (p=0.024) and 12 cpd (p=0.025) for photopic conditions for Group 2. At six months, statistically significant improvements in CS were noted across a substantially broader set of spatial frequencies, most notably under mesopic conditions, for Group 2, Mesopic CS at 6 CPD improved significantly for Group 1 at 6 months (p<0.05). Repeated measures ANOVA confirms the improvements in contrast sensitivity to be statistically significant across all study visits for at least 3 of the 5 spatial frequencies tested under mesopic and photopic conditions. A detailed summary of contrast sensitivity results are provided in Table 16.

TABLE 16

Contrast sensitivity change and significance levels at each spatial frequency tested under mesopic and photopic conditions

| Group Intervention | Contrast sensitivity at baseline | Contrast sensitivity at six months | T Test p* | RM ANOVA p** |
|---|---|---|---|---|
| | Photopic at 1.5 cpd | Photopic at 1.5 cpd | | |
| 20 mg L; 2 mg Z | 44 ± 26 | 53 ± 20 | 0.05 | 0.12 |
| 10 mg MZ; 10 mg L; 2 mg Z | 49 ± 30 | 68 ± 28 | 0.07 | 0.12 |
| Placebo | 52 ± 22 | 62 ± 29 | 0.41 | 0.28 |
| | Photopic at 3.0 cpd | Photopic at 3.0 cpd | | |
| 20 mg L; 2 mg Z | 85 ± 37 | 85 ± 29 | 0.96 | 0.68 |
| 10 mg MZ; 10 mg L; 2 mg Z | 73 ± 25 | 100 ± 28 | 0.002 | 0.002 |
| Placebo | 95 ± 36 | 94 ± 46 | 0.84 | 0.81 |
| | Photopic at 6.0 cpd | Photopic at 6.0 cpd | | |
| 20 mg L; 2 mg Z | 99 ± 27 | 100 ± 28 | 0.71 | 0.43 |
| 10 mg MZ; 10 mg L; 2 mg Z | 95 ± 36 | 114 ± 45 | 0.23 | 0.26 |
| Placebo | 103 ± 54 | 116 ± 64 | 0.83 | 0.88 |

TABLE 16-continued

Contrast sensitivity change and significance levels at each spatial frequency tested under mesopic and photopic conditions

| Group Intervention | Contrast sensitivity at baseline | Contrast sensitivity at six months | T Test p* | RM ANOVA p** |
|---|---|---|---|---|
| Photopic at 12.0 cpd | Photopic at 12.0 cpd | | | |
| 20 mg L; 2 mg Z | 30 ± 10 | 39 ± 17 | 0.178 | 0.26 |
| 10 mg MZ; 10 mg L; 2 mg Z | 32 ± 13 | 50 ± 30 | 0.011 | 0.008 |
| Placebo | 57 ± 43 | 62 ± 42 | 0.643 | 0.92 |
| Photopic at 18.0 cpd | Photopic at 18.0 cpd | | | |
| 20 mg L; 2 mg Z | 8 ± 5 | 12 ± 9 | 0.168 | 0.38 |
| 10 mg MZ; 10 mg L; 2 mg Z | 12 ± 6 | 23 ± 17 | 0.059 | 0.042 |
| Placebo | 20 ± 17 | 17 ± 14 | 0.527 | 0.73 |
| Mesopic at 1.5 cpd | Mesopic at 1.5 cpd | | | |
| 20 mg L; 2 mg Z | 57 ± 30 | 63 ± 23 | 0.618 | 0.83 |
| 10 mg MZ; 10 mg L; 2 mg Z | 52 ± 18 | 76 ± 24 | 0.003 | 0.000 |
| Placebo | 65 ± 27 | 75 ± 24 | 0.201 | 0.24 |
| Mesopic at 3.0 cpd | Mesopic at 3.0 cpd | | | |
| 20 mg L; 2 mg Z | 78 ± 45 | 74 ± 35 | 0.792 | 0.91 |
| 10 mg MZ; 10 mg L; 2 mg Z | 58 ± 17 | 88 ± 38 | 0.003 | 0.001 |
| Placebo | 68 ± 39 | 96 ± 44 | 0.101 | 0.11 |
| Mesopic at 6.0 cpd | Mesopic at 6.0 cpd | | | |
| 20 mg L; 2 mg Z | 41 ± 13 | 53 ± 21 | 0.06 | 0.004 |
| 10 mg MZ; 10 mg L; 2 mg Z | 50 ± 19 | 77 ± 49 | 0.14 | 0.058 |
| Placebo | 53 ± 46 | 63 ± 43 | 0.58 | 0.82 |
| Mesopic at 12.0 cpd | Mesopic at 12.0 cpd | | | |
| 20 mg L; 2 mg Z | 7 ± 4 | 9 ± 6 | 0.198 | 0.16 |
| 10 mg MZ; 10 mg L; 2 mg Z | 10 ± 6 | 33 ± 30 | 0.040 | 0.01 |
| Placebo | 13 ± 14 | 21 ± 25 | 0.400 | 0.50 |
| Mesopic at 18.0 cpd | Mesopic at 18.0 cpd | | | |
| 20 mg L; 2 mg Z | 2 ± 0 | 2 ± 0 | NS | 0.17 |
| 10 mg MZ; 10 mg L; 2 mg Z | 2 ± 9 | 11 ± 14 | 0.047 | 0.021 |
| Placebo | 4 ± 5 | 5 ± 3 | 0.593 | 0.28 |

RM ANOVA—Repeated measures ANOVA across all study visits;
NS—non significant (statistic not computed as SE of difference = 0)
*difference between baseline and 6 months (paired samples t test)
**repeated measures ANOVA across all visits
Group 1: n = 11;
Group 2: n = 11;
Group 3: n = 10

5. Glare Disability

Mesopic and photopic glare disability improved from baseline across a range of spatial frequencies at three months and at six months. At three months, statistically significant improvements were noted at 12 cpd (p=0.048) for mesopic conditions, and at 1.5 cpd (p=0.023) and 3 cpd (p=0.033) for photopic conditions for Group 2. At six months, statistically significant improvements were noted across a substantially broader set of spatial frequencies for Group 2. Repeated measures ANOVA across all study visits reveals no statistically significant change, at any spatial frequency, in mesopic or photopic glare disability for Groups 1 and 3. The statistically significant improvements in glare disability for Group 2, under both mesopic and photopic conditions, for all spatial frequencies tested (other than 18 cpd) were robust to repeated measures ANOVA. A detailed summary of glare disability results are provided in Table 17.

TABLE 17

Glare disability change and significance levels at each spatial frequency tested under mesopic and photopic conditions

| Group Intervention | Glare Disability at baseline | Glare Disability at six months | T test p* | RM ANOVA p** |
|---|---|---|---|---|
| Photopic at 1.5 cpd | Photopic at 1.5 cpd | | | |
| Group 1: 20 mg L; 2 mg Z | 56 ± 27 | 67 ± 20 | 0.056 | 0.12 |
| Group 2: 10 mg MZ; 10 mg L; 2 mg Z | 50 ± 22 | 67 ± 22 | 0.059 | 0.033 |
| Group 3: Placebo | 60 ± 25 | 74 ± 29 | 0.134 | 0.24 |
| Photopic at 3.0 cpd | Photopic at 3.0 cpd | | | |
| Group 1: 20 mg L; 2 mg Z | 84 ± 26 | 95 ± 31 | 0.175 | 0.28 |
| Group 2: 10 mg MZ; 10 mg L; 2 mg Z | 86 ± 24 | 121 ± 34 | 0.003 | 0.002 |
| Group 3: Placebo | 96 ± 30 | 97 ± 44 | 0.964 | 0.92 |
| Photopic at 6.0 cpd | Photopic at 6.0 cpd | | | |
| Group 1: 20 mg L; 2 mg Z | 114 ± 43 | 96 ± 37 | 0.181 | 0.26 |
| Group 2: 10 mg MZ; 10 mg L; 2 mg Z | 91 ± 39 | 130 ± 40 | 0.032 | 0.04 |
| Group 3: Placebo | 105 ± 51 | 112 ± 58 | 0.644 | 0.80 |
| Photopic at 12.0 cpd | Photopic at 12.0 cpd | | | |
| Group 1: 20 mg L; 2 mg Z | 34 ± 13 | 32 ± 14 | 0.785 | 0.13 |
| Group 2: 10 mg MZ; 10 mg L; 2 mg Z | 42 ± 20 | 70 ± 25 | 0.004 | 0.006 |
| Group 3: Placebo | 29 ± 21 | 62 ± 48 | 0.06 | 0.13 |
| Photopic at 18.0 cpd | Photopic at 18.0 cpd | | | |
| Group 1: 20 mg L; 2 mg Z | 17 ± 11 | 23 ± 12 | 0.35 | 0.08 |
| Group 2: 10 mg MZ; 10 mg L; 2 mg Z | 33 ± 13 | 65 ± 20 | 0.17 | 0.23 |
| Group 3: Placebo | 33 ± 15 | 46 ± 22 | 0.41 | 0.75 |
| Mesopic at 1.5 cpd | Mesopic at 1.5 cpd | | | |
| Group 1: 20 mg L; 2 mg Z | 23 ± 8 | 45 ± 35 | 0.08 | 0.05 |
| Group 2: 10 mg MZ; 10 mg L; 2 mg Z | 39 ± 26 | 58 ± 29 | 0.08 | 0.04 |
| Group 3: Placebo | 32 ± 24 | 38 ± 23 | 0.76 | 0.25 |
| Mesopic at 3.0 cpd | Mesopic at 3.0 cpd | | | |
| Group 1: 20 mg L; 2 mg Z | 36 ± 10 | 61 ± 43 | 0.066 | 0.06 |
| Group 2: 10 mg MZ; 10 mg L; 2 mg Z | 40 ± 14 | 74 ± 40 | 0.009 | 0.02 |
| Group 3: Placebo | 54 ± 39 | 59 ± 46 | 0.820 | 0.93 |
| Mesopic at 6 cpd | Mesopic at 6 cpd | | | |
| Group 1: 20 mg L; 2 mg Z | 64 ± 41 | 90 ± 53 | 0.15 | 0.17 |
| Group 2: 10 mg MZ; 10 mg L; 2 mg Z | 50 ± 19 | 77 ± 49 | 0.07 | 0.049 |
| Group 3: Placebo | 53 ± 46 | 64 ± 43 | 0.66 | 0.71 |
| Mesopic at 12 cpd | Mesopic at 12 cpd | | | |
| Group 1: 20 mg L; 2 mg Z | 5 ± 2 | 10 ± 17 | 0.303 | 0.35 |
| Group 2: 10 mg MZ; 10 mg L; 2 mg Z | 5 ± 2 | 12 ± 8 | 0.016 | 0.014 |
| Group 3: Placebo | 7 ± 5 | 10 ± 7 | 0.238 | 0.15 |
| Mesopic at 18 cpd | Mesopic at 18 cpd | | | |
| Group 1: 20 mg L; 2 mg Z | 2 ± 0 | 2 ± 0 | 0.34 | 0.44 |
| Group 2: 10 mg MZ; 10 mg L; 2 mg Z | 2 ± 1 | 11 ± 13 | 0.16 | 0.21 |
| Group 3: Placebo | 4 ± 5 | 5 ± 3 | 0.14 | 0.22 | cpd—Cycles per degree
*difference between baseline and 6 months (paired samples t test)
**repeated measures ANOVA across all visits
Group 1: n = 11;
Group 2: n = 11;
Group 3: n = 10

6. Photostress Recovery Time

Photostress recovery time did not improve significantly for any of the Groups during the study period (p>0.05 for all). Paired t test analysis revealed, however, that the improvement in PRT for Group 2 (PRT 37 seconds [or 21%] shorter on average at six months compared to baseline) approached, but did not reach statistical significance (t=2.067, p=0.069).

Ocular straylight measures did not change significantly for any Group (p>0.05 for all). Visual experience and ocular discomfort, as determined by questionnaire and discomfort rating, did not change significantly during the study period for any Group.

7. Comparison of Changes in MP with Changes in Visual Performance Parameters

A comparison was made between changes in macular pigment and changes in visual performance parameters between baseline and 6 months. There was no statistically significant relationship between change in macular pigment and any of the visual performance variables (p>0.05 for all). Table 18 gives the results for photopic (daytime) and mesopic (night-time) contrast sensitivity at 1.5 cpd.

TABLE 18

Changes in macular pigment (at 0.25° eccentricity) compared with changes in the following visual performance parameters between baseline and 6 months : BCVA, photopic (daytime) contrast sensitivity, mesopic (night-time) contrast sensitivity, photopic contrast sensitivity under glare conditions, mesopic contrast sensitivity under glare conditions.

|  | r | p |
|---|---|---|
| Change in MP vs change in BCVA | | |
| Group 1 (20 L, 2 Z) | −0.075 | 0.827 |
| Group 2 (10 L, 10 MZ, 2 Z) | 0.09 | 0.794 |
| Group 3 (placebo) | 0.119 | 0.743 |
| Change in MP vs change in photopic CS (1.5 cpd) | | |
| Group 1 (20 L, 2 Z) | −0.104 | 0.76 |
| Group 2 (10 L, 10 MZ, 2 Z) | −0.154 | 0.651 |
| Group 3 (placebo) | −0.242 | 0.5 |
| Change in MP vs change in mesopic CS (1.5 cpd) | | |
| Group 1 (20 L, 2 Z) | 0.394 | 0.231 |
| Group 2 (10 L, 10 MZ, 2 Z) | −0.082 | 0.81 |
| Group 3 (placebo) | −0.179 | 0.621 |
| Change in MP vs change in photopic GD (1.5 cpd) | | |
| Group 1 (20 L, 2 Z) | −0.348 | 0.294 |
| Group 2 (10 L, 10 MZ, 2 Z) | 0.263 | 0.435 |
| Group 3 (placebo) | 0.331 | 0.351 |
| Change in MP vs change in mesopic GD (1.5 cpd) | | |
| Group 1 (20 L, 2 Z) | 0.394 | 0.231 |
| Group 2 (10 L, 10 MZ, 2 Z) | −0.082 | 0.81 |
| Group 3 (placebo) | −0.179 | 0.621 |

Abbreviations: MP = macular pigment; BCVA = best corrected visual acuity; L = lutein; Z = zeaxanthin; MZ = meso-zeaxanthin; CS = contrast sensitivity; cpd = cycles per degree; GD = glare disability.

Surprisingly, these data show that the observed increases in visual performance parameters were independent of the increases in macular pigment.

Discussion

In terms of MPOD, there was no significant change at any eccentricity, at 3 or at 6 months, in subjects supplemented with a preparation that does not contain MZ or in subjects given placebo. In contrast, subjects supplemented with all three macular carotenoids exhibited a significant increase in MPOD at 4 of the 5 eccentricities tested, at 3 months and at 6 months.

The current study demonstrates a novel and important effect of MP augmentation on visual performance among healthy subjects without ocular disease. Across a broad range of testing modalities and conditions, visual performance improved significantly among subjects who exhibited a significant rise in MPOD. Specifically, improvements in contrast sensitivity and glare disability (across virtually all spatial frequencies, and under daytime and nighttime conditions), and improvements in visual acuity, were demonstrated in subjects supplement with all three macular carotenoids, but no such observations were seen in the placebo control subjects or in subjects supplemented with L and Z (but not MZ).

The data support the view that MP may influence visual performance through its optical filtration effects, as the glare disability test protocol included an LED glare source that exhibited a short wavelength peak emission profile matching the known spectral absorbance of MP. The observed improvements in acuity and contrast sensitivity, however, are less consistent with a solely optical explanation. The stimuli used do, however, contain a relatively small short wavelength component. It is possible, therefore, that MP augmentation results in optical image enhancement through a reduction of the deleterious effects of chromatic aberration and light scatter, and thereby improves visual acuity and contrast sensitivity, even for such spectrally broadband stimuli. It is also possible that the macular carotenoids, which are intracellular compounds, also play a neurobiological role, thereby contributing to, and/or facilitating, optimal neurophysiological performance, and hence visual function (the limits of spatial vision represent the combined influence of optical and neural efficiency limits). This view is supported by observation that there was no correlation between increases in visual performance and increases in macular pigment, suggesting that the MP carotenoids may exert effects on visual performance by a neuro-physiological mechanism.

In conclusion, we have demonstrated a rapid and sustained rise in MPOD following supplementation with all three macular carotenoids, and this was not observed in placebo-controlled subjects or in subjects supplemented with a preparation lacking MZ. Further, supplementation with all three macular carotenoids resulted in significant improvements in contrast sensitivity and glare disability (under photopic and scotopic conditions) and in corrected distance visual acuity, whereas no such changes were seen in placebo controls or in subjects supplemented with a preparation lacking MZ. These findings have potentially important implications for people engaged in activities where optimization of visual importance is important (especially if operating under bright conditions), and warrant further study.

EXAMPLE 5

Effect of a Supplement Containing MZ on Visual Performance in Subjects with an Atypical Distribution of Macular Pigment (a Central Dip)

Subjects and Dosage

Eight subjects with pre-identified central dips in their macular pigment spatial profile as described in example 2 were recruited into this study. All eight subjects consumed a supplement containing 10 mg L, 10 mg MZ, and 10 mg Z daily for 3 months.

Methods

Macular pigment optical density (MPOD) was measured as in Example 1 at baseline and after 3 months of MZ supplementation. Letter contrast sensitivity (Thomson Chart) was likewise measured using the method described in Example 3 section 4

Results

Figure 10:
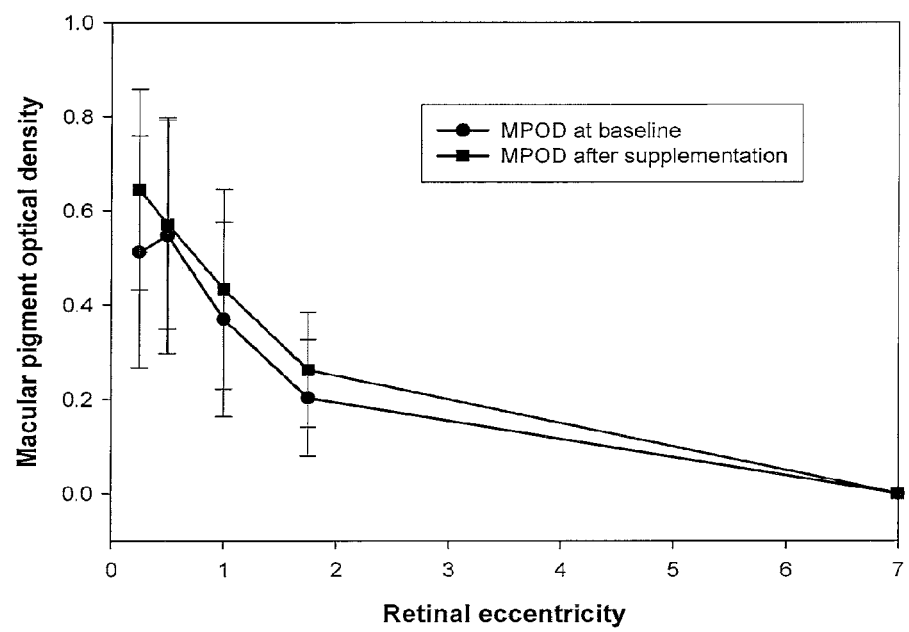
FIG. 10 is a graph of MPOD against retinal eccentricity (mean of eight subjects; see example 5) before (circular symbols) or after (square symbols) 3 months of supplementation with a daily dose of 10 mg L, 10 mg MZ and 10 mg Z.

1. MPOD results: As seen from Table 19 and FIG. 10, the spatial profile of MP was normalised following supplementation with 10 mg L, 10 mg MZ, and 10 mg Z for 3 months. All subjects responded to this intervention. Statistically significant increases were seen at all eccentricities except for 0.5°.

TABLE 19

| Eccentricity | Baseline | 3 months | p |
|---|---|---|---|
| 0.25° | 0.51 ± 0.25 | 0.64 ± 0.21 | <0.001 |
| 0.5° | 0.54 ± 0.25 | 0.57 ± 0.20 | 0.140 |
| 1° | 0.37 ± 0.20 | 0.43 ± 0.21 | 0.016 |
| 1.75° | 0.20 ± 0.12 | 0.26 ± 0.12 | 0.008 |

2. Contrast sensitivity: as seen from Table 20 there was an improvement in contrast sensitivity following supplementation with 10 mg L, 10 mg MZ, and 10 mg Z for 3 months.

TABLE 20

| Contrast sensitivity | Baseline | 3 months | p |
|---|---|---|---|
| 1.2 cpd | 2.00 ± 0.15 | 2.07 ± 0.12 | 0.103 |
| 2.4 cpd | 1.86 ± 0.16 | 2.02 ± 0.19 | 0.003 |
| 6 cpd | 1.56 ± 0.19 | 1.71 ± 0.21 | <0.001 |
| 9.6 cpd | 1.34 ± 0.21 | 1.46 ± 0.18 | 0.051 |
| 15.15 cpd | 1.02 ± 0.16 | 1.11 ± 0.20 | 0.035 |

EXAMPLE 6

In one embodiment, the composition of the invention takes the form of a mineral- and vitamin-containing dietary supplement, augmented with MZ, L and, optionally Z. The supplement is formulated as a tablet, with the following composition of active ingredients:—

| | |
|---|---|
| MZ | 5 mg |
| L | 5 mg |
| Z | 1 mg |
| Vitamin A | 800 micrograms |
| Thiamin | 1.1 mg |
| Riboflavin | 1.4 mg |
| Vitamin B6 | 2.0 mg |
| Vitamin B12 | 2.5 micrograms |
| Folic acid | 400 micrograms |
| Niacin | 20 mg |
| Pantothenic Acid | 6 mg |
| Biotin | 50 micrograms |
| Vitamin C | 80 mg |
| Vitamin D | 20 micrograms |
| Vitamin E | 12 mg |
| Calcium | 120 mg |
| Magnesium | 60 mg |
| Iron | 14 mg |
| Zinc | 10 mg |
| Copper | 1 mg |
| Iodine | 150 micrograms |
| Manganese | 3 mg |
| Chromium | 40 micrograms |
| Selenium | 55 micrograms |
| Molybdenum | 50 micrograms |

The following ingredients may be used as a source of the minerals and vitamins.

Minerals: calcium carbonate, magnesium hydroxide, ferrous fumarate, zinc oxide, copper sulphate, potassium iodide, manganese sulphate, chromic chloride, sodium selenate, sodium molybdate.

Vitamins: Retinyl acetate, Thiamin mono nitrate, Riboflavin, Pyridoxin hydrochloride, Cyano cobalomin, Folic Acid, Niacin, Calciun-D-pantothenate, D-biotin, Sodium Ascorbate#, Cholecalciferol, D-alpha-tocopherol acetate The tablets may conveniently additionally comprise one or more of the following fillers: Malto dextrin, Microcellulose, Hydroxy propyl methyl cellulose, Shellac, Talcum, Gum acacia, Glycerol, Titanium dioxide, Polyfructose One tablet (e.g. 500 mg) to be taken per day.

EXAMPLE 7

Provision of MZ in Egg Yolks for Human Consumption

Several workers have shown that uptake of L and Z from egg yolks is 2-4 times more efficient than from capsules (Handleman et al, 1999 Am. J. Clin. Nutr. 70, 247-251; Goodrow et al., 2006 J. Nutr. 136, 2519-2524; Johnson 2004, J. Nutr. 134, 1887-1893).

The objective of this study was to feed hens a mixture of L, MZ and Z to determine the total amount of MZ in the yolk. In addition 24 eggs collected at the end of the experiment were consumed by one subject, one egg/day and the blood MZ composition determined.

Methods

Eight Bovan Goldline hens were obtained at approximately 18 weeks of age.

When the hens were producing at least 8 eggs per day in total, the hens were isolated and fed only a commercial meal. The experiment was started 1 week later when a premix containing the mixed carotenoids was added to the meal. The premix provided 250 mg MZ/kg feed with proportions of L 50, MZ 30, Z 20.

The yolk carotenoids were measured in mixtures prepared from all eggs collected at baseline, three and six weeks.

Preparation of Egg-Yolk Suspensions

Yolks were individually weighed and mixed with phosphate-buffered saline and made up to 50 ml. Two ml of each suspension was mixed in a separate universal tube for each of the three batches separately and stored at −40 C.

Carotenoid Extraction (i) Egg Yolk Suspensions

The egg yolk suspension (0.1 ml) was mixed with 0.15 ml aqueous KOH (25 g/100 ml water), 0.15 ml absolute ethyl alcohol and 0.1 ml echinenone (internal standard, 0.4 mg/500 ml ethyl alcohol) in a glass extraction tube and incubated at 45 C for 45 minutes.

Solutions were then cooled and mixed vigorously with 1.5 ml hexane (containing BHT500 mg/l) and centrifuged to separate the hexane and aqueous layers. One ml of the upper hexane layer was transferred to an evaporating tube and the residue was re-extracted with 1.5 ml hexane. After centrifuging, 1.5 ml of the upper layer was removed and the extracts combined and evaporated to dryness under nitrogen at 40 C. The residue was made up to 0.15 ml with mobile phase (see Ultracarb HPLC below) and 0.1 ml was injected onto a Ultra Carb Column for HLPC analysis.

(ii) Plasma

Blood (10 ml) from a human subject was collected in lithium heparin tubes at baseline, day 12 and day 24 after consumption of one egg per day and centrifuged to provide plasma subsequently stored at −40 C. Plasma, 0.25 ml was mixed with 0.2 ml sodium dodecyl sulphate, 0.4 ml ethyl acetate (internal standard). Hexane containing BHT (1.0 ml) was added and the mixture extracted vigorously for 4 minutes, centrifuged for 10 mins and 0.7 ml of the upper hexane layer removed and evaporated to dryness.

The residue was made up to 0.1 ml with mobile phase (see HPLC procedure below) and 0.05 ml was injected onto the column.

Liquid Chromatography (HPLC) to Measure L, MZ, Z

Separation and quantitation of the MZ was achieved using a two column procedure.

Ultracarb Procedure: Extracts prepared as described above were reconstituted in a mobile phase comprising acetonitrile:methanol (85:15 containing 0.1% triethylamine) Using the same solvent mixture at 1.5 ml/min, extracts were chromatographed isocratically using a 3 micro m Ultracarb ODS column (250×4.6 mm, Phenomenex, UK) and detected using a photodiode-array detector (model 2996, Waters Ltd) to quantify L and Z+MZ at 450 nm. Eluent that coincided with the emergence of MZ+Z was collected from the waste line and evaporated to dryness under nitrogen.

Chiral Chromoatography: The Z+MZ extract was then reconstituted in 0.1 ml of hexane:isopropanol (90:10) and 50 uL was chromatographed on a 10 micro m Chiralpak®AD column (250×4.6 mm; Chiral Technologies Europe, 67404 Illkirch Cedex, France) to determine the proportion of MZ and Z isomers using gradient elution at 0.8 ml/min starting with 90% hexane and 10% isopropyl alcohol and increasing to 95% hexane in a linear gradient over 30 minutes.

Results

MZ in Egg Yolks

Mean (SD) weights of the yolks at baseline and at the end of weeks 3 and 6 were 12.29 (0.35), 14.23 (0.87) and 15.73 (0.72) g respectively. The MZ contents of the yolks are shown in Table 21. At baseline only L and Z were present;

Feeding 250 ppm of the carotenoid mixture for 3 weeks produced egg yolks containing 2.78 mg MZ/yolk of which L was circa 76% Z 13% and MZ 11%. There was no further increase at 6 weeks Plasma The MZ content in plasma from one human subject consuming one egg per day are shown in table 22.

Baseline total MZ concentration was 0.81 micro mol/litre of which L was 53% Z was 47% and MZ 0%. The concentration of L had almost trebled at day 12 but the concentration then fell to only double the baseline value at day 24.

The increase in MZ+Z at days 12 and 24 was 30% and 23% respectively and was due solely due to increase in MZ.

Conclusions

Feeding a mixture of carotenoids to chickens for 3 and 6 weeks increased L+MZ+Z in the egg yolks and in plasma in a subject consuming one egg per day.

The MZ content per yolk was raised from circa 0.8 mg to 2.8 mg. Since it is known that the absorption of L and Z from egg yolk is enhanced, two or three eggs from chickens fed a mixture of L, Z and MZ could provide sufficient MZ to improve visual performance in the subject, although this was not tested.

TABLE 21

MZ contents of egg yolks from chicken fed 250 mg/kg mixed carotenoids micro grams per yolk

| Weeks | L | Z | MZ | Total |
|---|---|---|---|---|
| 0 | 563 | 278 | 0 | 841 |
| 3 | 2100 | 366 | 315 | 2781 |
| 6 | 2260 | 328 | 272 | 2860 |

TABLE 22

MZ contents of plasma in one person consuming one egg per day (units are micro moles per liter).

| Day | L | Z | MZ | Total |
|---|---|---|---|---|
| 0 | 0.55 | 0.26 | 0 | 0.81 |
| 12 | 1.20 | 0.28 | 0.06 | 1.54 |
| 24 | 1.06 | 0.25 | 0.07 | 1.38 |

EXAMPLE 8

The Addition of MZ to Dietary Formulations and VP

A dry powder formula dietary supplement composition can be prepared by mixing 5 mg MZ, 5 mg L and 1 mg Z with the contents of 4 sachets containing circa 50 g each of "The Cambridge Diet" product, obtained from Cambridge Nutritional Foods Limited, Stafford House, Brakey Road, Corby NN17 SLU, United Kingdom (The Cambridge Diet is a registered trade mark).

EXAMPLE 9

Fish Oils, MZ and VP

The retina contain a high concentration of Omega 3 fatty acids which are especially abundant in fish oils, for example oils from salmon, herring, mackerel, anchovies, sardines; also from krill and green-lipped muscles. Omega 3 fatty acids are found as eicosapentanoic acid $C_{22.6n-3}$ (EPA) and docosahexanoic acid $C_{22.6n-3}$ (DHA) and combined make up about 30% of fish body oil. The acceptable daily macro nutrient dose (AMND) of EPA+DHA is about 1.6 g/day for men and 1.1 g/day for women, i.e. about 5 g and 3.5 g fish oil respectively.

The occurrence of a high concentration of omega 3 fatty acids in the retina suggests that they may play and important role in vision. A combination of macular carotenoids (MC) containing MZ with omega3 fatty acids would thus be beneficial to the retina and improve visual performance. The mixture can be in capsules or as an emulsion in a sachet. The latter has the advantage that fewer doses can be given in a sachet whilst several large capsules (which many elderly people find difficult to swallow) are needed for the AMND. The emulsion can contain from 25-60% fish oils to provide from 0.5-2.0 g omega-3 fatty acids and sufficient MC to give a daily dose of 0.5 mg to 50 mg MC per day.

A commercial preparation of active macular carotenoids (MC) consisting of mesozeazanthin 10 g lutein 10 g and zeaxanthin 2 g in 78 ml krill oil is mixed with 900 ml salmon oil and made into soft gel capsules each containing 1 g oil formulation. A daily dose of 5 capsules will provide the 1.5 g of Omega 3 fatty acids and a 22 mg dose of macular carotenoids to improve visual performance.

An alternative embodiment may be formulated as follows:

Ingredients

| | |
|---|---|
| The mixture of and MC, krill and salmon oils as above | 55% |
| Water | 35% |
| Sucralose (Splenda ™) | 4% |
| Milk powder | 5% |
| Potassium sorbate | 0.1% |

| -continued | |
|---|---|
| Alpha tocopherol | 0.1% |
| Flavorings (e.g. citrus) | 0.8% |

An emulsion is made under an inert atmosphere using standard techniques and then packed into airtight sachets each containing 5 grams emulsion. The daily dose is 2 sachets per day containing 6 g omega 3 fatty acids and 22 mg MC.

The invention claimed is:

1. A capsule consisting essentially of isolated mesozeaxanthin, isolated lutein, isolated zeaxathin, and krill oil.

* * * * *